(12) United States Patent
Dobrinsky et al.

(10) Patent No.: US 10,881,755 B2
(45) Date of Patent: Jan. 5, 2021

(54) ULTRAVIOLET ILLUMINATION WITH OPTICAL ELEMENTS

(71) Applicant: Sensor Electronic Technology, Inc., Columbia, SC (US)

(72) Inventors: Alexander Dobrinsky, Silver Spring, MD (US); Maxim S. Shatalov, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/236,870

(22) Filed: Dec. 31, 2018

(65) Prior Publication Data

US 2019/0201570 A1 Jul. 4, 2019

Related U.S. Application Data

(60) Provisional application No. 62/681,859, filed on Jun. 7, 2018, provisional application No. 62/612,508, filed on Dec. 31, 2017.

(51) Int. Cl.
*A61L 2/24* (2006.01)
*A61L 2/10* (2006.01)
(Continued)

(52) U.S. Cl.
CPC .............. *A61L 2/24* (2013.01); *A23B 7/015* (2013.01); *A23L 3/28* (2013.01); *A61L 2/10* (2013.01); *G01N 21/645* (2013.01); *G01N 21/8806* (2013.01); *G01N 21/94* (2013.01); *G01N 33/025* (2013.01); *A23V 2002/00* (2013.01);
(Continued)

(58) Field of Classification Search
CPC .... A61L 2/10; A61L 2202/11; A61L 2209/12; A61L 2/0047; A61L 9/20; A61L 2/24; A61L 2202/16; A61L 2202/14; A61L 2202/122; C02F 1/325; C02F 1/32; C02F 2201/326; A23L 3/28; A23B 7/015; G01N 33/025; G01N 21/94; G01N 21/645; G01N 21/8806; G01N 2021/646; G01N 2201/0636; G01N 2021/6463; A23V 2002/00
See application file for complete search history.

(56) References Cited

U.S. PATENT DOCUMENTS 7,553,456 B2 6/2009 Gaska et al.
7,634,996 B2 12/2009 Gaska et al.
(Continued)

*Primary Examiner* — Brooke Purinton
(74) *Attorney, Agent, or Firm* — LaBatt, LLC

(57) ABSTRACT

Ultraviolet illumination with optical elements to irradiate objects and/or fluid for purposes of sterilization, disinfection, and/or cleaning. The objects and/or fluid can be irradiated using an ultraviolet illuminator having at least one ultraviolet light emitting source. An ultraviolet transparent housing encapsulates the at least one ultraviolet light emitting source. The ultraviolet transparent housing includes an ultraviolet transparent material that emits ultraviolet light from the at least one ultraviolet light emitting source while preventing humidity from penetrating the ultraviolet transparent housing and damaging the at least one ultraviolet light emitting source. At least one ultraviolet transparent optical element is located about the ultraviolet transparent housing interspersed with the ultraviolet transparent material.

20 Claims, 7 Drawing Sheets

(51) Int. Cl.
  *G01N 21/88* (2006.01)
  *G01N 21/64* (2006.01)
  *G01N 21/94* (2006.01)
  *G01N 33/02* (2006.01)
  *A23B 7/015* (2006.01)
  *A23L 3/28* (2006.01)

(52) U.S. Cl.
  CPC ...... *A61L 2202/11* (2013.01); *A61L 2202/122* (2013.01); *A61L 2202/14* (2013.01); *A61L 2202/16* (2013.01); *G01N 2021/646* (2013.01); *G01N 2021/6463* (2013.01); *G01N 2201/0636* (2013.01)

(56) References Cited

U.S. PATENT DOCUMENTS

| | | | |
|---|---|---|---|
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |
| 9,138,499 B2 | 9/2015 | Bettles et al. | |
| 9,179,703 B2 | 11/2015 | Shur et al. | |
| 9,339,571 B2 * | 5/2016 | Bilenko | A61L 2/10 |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,707,307 B2 | 7/2017 | Shur et al. | |
| 9,718,706 B2 | 8/2017 | Smetona et al. | |
| 9,724,441 B2 | 8/2017 | Shur et al. | |
| 9,750,830 B2 | 9/2017 | Shur et al. | |
| 9,757,486 B2 | 9/2017 | Dobrinsky et al. | |
| 9,764,050 B1 * | 9/2017 | Almeida | A61L 2/10 |
| 9,795,699 B2 | 10/2017 | Shur et al. | |
| 9,801,965 B2 | 10/2017 | Bettles et al. | |
| 9,802,840 B2 | 10/2017 | Shturm et al. | |
| 9,878,061 B2 | 1/2018 | Shur et al. | |
| 9,919,068 B2 | 3/2018 | Shur et al. | |
| 9,974,877 B2 | 5/2018 | Bettles et al. | |
| 9,981,051 B2 | 5/2018 | Shur et al. | |
| 9,987,383 B2 | 6/2018 | Bilenko et al. | |
| 9,999,782 B2 | 6/2018 | Shur et al. | |
| 10,004,821 B2 | 6/2018 | Dobrinsky et al. | |
| 10,040,699 B2 | 8/2018 | Smetona et al. | |
| 10,099,944 B2 | 10/2018 | Smetona et al. | |
| 2005/0077482 A1 * | 4/2005 | Poppi | A61L 2/10 250/492.1 |
| 2011/0011112 A1 * | 1/2011 | Goel | A61L 9/20 62/264 |
| 2012/0199005 A1 * | 8/2012 | Koji | A61L 9/205 96/224 |
| 2012/0305787 A1 * | 12/2012 | Henson | A61L 2/10 250/372 |
| 2013/0048545 A1 | 2/2013 | Shatalov et al. | |
| 2014/0202962 A1 | 7/2014 | Bilenko et al. | |
| 2015/0258228 A1 * | 9/2015 | Cohen | A61L 2/10 345/178 |
| 2016/0074547 A1 * | 3/2016 | Dobrinsky | A61L 2/10 250/492.1 |
| 2016/0106873 A1 * | 4/2016 | Dobrinsky | A61L 9/00 250/393 |
| 2016/0114186 A1 | 4/2016 | Dobrinsky et al. | |
| 2017/0057842 A1 | 3/2017 | Dobrinsky et al. | |
| 2017/0100495 A1 | 4/2017 | Shur et al. | |
| 2017/0189711 A1 | 7/2017 | Shur et al. | |
| 2017/0245527 A1 | 8/2017 | Dobrinsky et al. | |
| 2017/0245616 A1 | 8/2017 | Lakios et al. | |
| 2017/0281812 A1 | 10/2017 | Dobrinsky et al. | |
| 2017/0290934 A1 | 10/2017 | Dobrinsky et al. | |
| 2017/0368215 A1 | 12/2017 | Shatalov et al. | |
| 2018/0028700 A1 | 2/2018 | Dobrinsky et al. | |
| 2018/0092308 A1 | 4/2018 | Dobrinsky et al. | |
| 2018/0104368 A1 | 4/2018 | Dobrinsky et al. | |
| 2018/0117194 A1 | 5/2018 | Dobrinsky et al. | |
| 2018/0185529 A1 | 7/2018 | Shur et al. | |
| 2018/0221521 A1 | 8/2018 | Shur et al. | |
| 2018/0243458 A1 | 8/2018 | Shatalov et al. | |
| 2018/0269022 A1 * | 9/2018 | Tiren | H01J 65/046 |
| 2018/0339075 A1 | 11/2018 | Kennedy et al. | |
| 2019/0030477 A1 | 1/2019 | Shatalov | |
| 2019/0098842 A1 | 4/2019 | Barber, III et al. | |
| 2019/0099613 A1 | 4/2019 | Estes et al. | |
| 2019/0100445 A1 | 4/2019 | Dobrinsky | |
| 2019/0100718 A1 | 4/2019 | Estes et al. | |
| 2019/0117811 A1 | 4/2019 | Barber, III | |
| 2019/0125907 A1 | 5/2019 | Dobrinsky | |
| 2019/0135659 A1 | 5/2019 | Smetona et al. | |

\* cited by examiner

ULTRAVIOLET ILLUMINATION WITH OPTICAL ELEMENTS

REFERENCE TO RELATED APPLICATIONS

The present patent application claims the benefit of U.S. Provisional Application No. 62/612,508, which was filed on 31 Dec. 2017, and U.S. Provisional Application No. 62/681,859, which was filed on 7 Jun. 2018, both of which are hereby incorporated by reference.

TECHNICAL FIELD

The disclosure relates generally to ultraviolet irradiation, and more specifically, to a solution for using ultraviolet radiation with optical elements to irradiate objects and/or fluids for purposes of sterilization, disinfection, and/or cleaning.

BACKGROUND ART

Ultraviolet water and air purification and surface sterilization systems are known and have a successful history of development. The main unit of these ultraviolet systems is a source of ultraviolet radiation having wavelength(s) close to the absorption peaks of biologically significant molecules of DNA and proteins. The systems can sterilize a medium to a safe condition providing the power of the ultraviolet radiation source and an exposure time are sufficient to destroy the internal biomolecular structure of bacteria, viruses, protozoa and germs.

Known ultraviolet surface sterilization systems typically use mercury lamps or deep ultraviolet light emitting diodes as a source of ultraviolet radiation. Low-pressure and medium-pressure mercury lamps provide a linear spectrum of radiation with some lines with wavelengths that are in the relative vicinity to a DNA absorption line. A low-pressure mercury lamp with a main peak at 253.4 nm is often used in low-consumption residential water and air purification systems. Medium-pressure mercury lamps with a higher radiation power have a multi-peak radiation spectrum and often are used in municipal systems with medium and high-water consumption.

However, the use of mercury lamps has significant drawbacks. For example, mercury lamps are fragile and bulky, and mercury is an extremely dangerous element, which implies serious limitations on applications of mercury-based water purification systems. In particular, mercury lamps are not practical for use in transport and individual systems. Furthermore, a typical operating lifetime of a mercury lamp is less than 10,000 hours. An additional limitation is an inability to adjust or control a radiation spectrum of the mercury lamp. To this extent, the peaks of a mercury lamp do not exactly coincide with the absorption peaks of DNA and proteins, thereby decreasing the sterilization efficiency.

Some approaches have sought to minimize one or more drawbacks of mercury lamp-based sterilization. For example, one approach proposes a handheld ultraviolet water purification system based on a miniature mercury lamp. The design is targeted to overcome the size and portability drawbacks of traditional mercury lamp-based ultraviolet purifying systems. Nevertheless, the need for contact and even steering the sterilizing water with a fragile quartz sleeve with the mercury lamp inside makes the device dangerous for residential applications and not appropriate for transport, field, and portable applications.

SUMMARY OF THE INVENTION

This Summary of the Invention introduces a selection of certain concepts in a brief form that are further described below in the Detailed Description of the Invention. It is not intended to exclusively identify key features or essential features of the claimed subject matter set forth in the Claims, nor is it intended as an aid in determining the scope of the claimed subject matter.

Aspects of the present invention are directed to solutions that use ultraviolet radiation with optical elements to irradiate objects and/or fluids for purposes of sterilization, disinfection, and/or cleaning. In the various embodiments, at least one ultraviolet radiation source such as an ultraviolet light emitting device can be used to irradiate a surface of an object and/or a fluid. An ultraviolet light emitting diode is one example of a type of ultraviolet light emitting device that can be used in the various embodiments. Use of one or more ultraviolet light emitting diodes allows an ultraviolet illuminator or an ultraviolet illumination system to have a significantly simplified design. For example, ultraviolet light emitting diodes offer robust technology which does not utilize high voltages which can be the case with other ultraviolet illuminators or ultraviolet illumination systems that employ mercury lamps. In addition, ultraviolet light emitting diodes can be easily turned on and off. Also, ultraviolet light emitting diodes do not require quartz enclosures which can be the case with other sources such as mercury lamps. Further, ultraviolet illuminators or ultraviolet illumination systems having ultraviolet light emitting diodes can be manufactured as small devices.

The ultraviolet light emitting diodes, like any of the other ultraviolet radiation sources of the various embodiments, can be configured to operate at peak wavelengths that facilitate sterilization, disinfection and general cleaning of objects that remove harmful contaminants, bacteria, parasites, micro-organisms and the like, as well as provide a similar treatment of fluids. In one embodiment, one or more of the ultraviolet light emitting diodes can be configured to generate ultraviolet C (UV-C) radiation at a set of peak wavelengths that range from 250 nm to 360 nm. In one embodiment, one or more of the ultraviolet light emitting diodes can be configured to generate ultraviolet A (UV-A) and/or visible radiation (also referred to as blue-UV radiation) at a set of peak wavelengths that range from 310 nm to 460 nm. In one embodiment, the ultraviolet light emitting diodes can be configured with some of the ultraviolet radiation sources generating UV-C radiation and other sources generating blue-UV radiation.

An ultraviolet transparent housing structure can be used to encapsulate the ultraviolet light emitting source(s). The ultraviolet light emitting source(s) can be movable about the ultraviolet transparent housing or permanently fixed, and configured to generate movable beam of light. The ultraviolet transparent housing can include an ultraviolet transparent material that emits ultraviolet light from the ultraviolet light emitting source(s) while preventing humidity from penetrating the ultraviolet transparent housing and damaging the source(s). In one embodiment, the ultraviolet transparent material can include an ultraviolet transparent film. The ultraviolet transparent film can cover at least one light emitting side of the source(s). In one embodiment, the ultraviolet transparent film can be formed in the housing in a location that is adjacent to the ultraviolet light emitting source(s). The ultraviolet transparent material of the ultraviolet transparent housing can also include a composite material. In one embodiment, the composite material can have a multilayered structure formed from a fluoropolymer having biofouling properties.

The ultraviolet transparent housing can take the form of one of a variety of configurations. In one embodiment, the ultraviolet transparent housing can have a cylinder-shaped structure. For example, the cylinder-shaped ultraviolet transparent housing can be configured as a mesh housing with a plurality of ultraviolet transparent windows integrated within an interlaced structure, with each ultraviolet transparent window configured to emit ultraviolet light there through. In one embodiment, the plurality of ultraviolet transparent windows can comprise an ultraviolet transparent fluoropolymer and the interlaced structure can comprise a polymer or a fluoropolymer.

At least one ultraviolet transparent optical element can be located about the ultraviolet transparent housing interspersed with the ultraviolet transparent material. The ultraviolet transparent optical element(s) can serve to focus ultraviolet radiation or light emitted from the ultraviolet light emitting source(s) to an object or a fluid for irradiation thereof. The ultraviolet transparent optical element(s) can include a lens element. Examples of a lens element can include, but are not limited to, a Fresnel lens and a total internal reflection (TIR) lens. In one embodiment, ultraviolet transparent optical element(s) can be configured as a set of lens elements. These lens elements can be formed from a fluoropolymer material.

In one embodiment, the ultraviolet transparent optical element(s) can comprise a primary set of optical elements and a secondary set of optical elements that can include any of the aforementioned lens elements. For example, the primary set of optical elements can be located at interface between the ultraviolet transparent material of the housing and the ultraviolet light emitting source(s), and the secondary set of optical elements can be located about (e.g., adjacent or in the proximity to) the source(s). In one embodiment, the primary set of optical elements can be encapsulated within the ultraviolet transparent housing with the at least one ultraviolet light emitting source(s), while the secondary set of optical elements can be formed on the exterior of housing (e.g., at an interface with the ultraviolet transparent material of the housing). In this manner, each of the primary and secondary optical elements can be optically coupled with the ultraviolet light emitting sources.

The ultraviolet transparent housing can include a set of structural elements that provide structural support for the housing to prevent a change in shape of the housing. For example, the set of structural elements can occupy at least 50% of an external surface area of the ultraviolet transparent housing. In one embodiment, the set of structural elements can include a set of ultraviolet transparent domains that form depressions or voids sunken below the external surface area of the ultraviolet transparent housing to define ultraviolet transparent cellular windows. Each of the ultraviolet transparent cellular windows can have ultraviolet transparent media enclosed by supporting walls that extend from the sunken depression up to the external surface area of the ultraviolet transparent housing. At least one of the supporting walls can have a reflective surface that is reflective to ultraviolet light to facilitate ultraviolet transmission through the ultraviolet transparent cellular window, as well as to promote recycling and light guiding of the radiation. In one embodiment, at least one of the supporting walls can have a diffusively reflective surface. The reflective surface(s) and the diffusively reflective surface(s) can be located at a lower portion of the supporting wall(s) adjoining the ultraviolet transparent cellular window. Each of the sunken ultraviolet transparent cellular windows surrounded by adjoining walls can take the form of a hexagonal bee-hive type cell configuration that can be implemented in a rounded cylindrical shaped structure or a non-rounded flat structure. In one embodiment, the ultraviolet transparent cellular windows can be separated a predetermined distance apart from the ultraviolet light emitting source(s).

The ultraviolet transparent domains of the ultraviolet transparent housing can have an ultraviolet transparent optical element formed there over. In this manner, the set of ultraviolet transparent domains and the ultraviolet transparent optical elements can operate cooperatively to focus ultraviolet light onto a surface of an object or at a fluid. With this configuration, the set of ultraviolet transparent domains and the ultraviolet transparent optical elements can illuminate the object or fluid with relatively uniform illumination (e.g., uniformity of illumination that is at least 30%). In one embodiment, some of the ultraviolet transparent domains can comprise an ultraviolet transparent optical element such as a lens formed there over, while others of the domains can be configured without such an optical element.

The ultraviolet transparent domains can be formed with one of a variety of different materials. For example, each of the ultraviolet transparent domains can have a different material. In one embodiment, the set of ultraviolet transparent domains can be optically connected by ultraviolet transparent wave guiding material that waveguides the ultraviolet light emitted from the ultraviolet light emitting source(s) along the ultraviolet transparent housing before emitting the radiation to the object or the fluid. In one scenario, the ultraviolet transparent wave guiding material can include a plurality of light scattering elements.

In one embodiment, the ultraviolet transparent housing can have a reflective element formed within an interior portion of the housing to direct ultraviolet light from the ultraviolet light emitting source(s) to the ultraviolet transparent cellular windows. The reflective element such as a mirror element can take the form of one of a variety of shapes that is suitable for placement within the interior portion of the housing. For example, the reflective element can include a cone-shaped element that optically couples the ultraviolet light emitting source(s) to the ultraviolet transparent cellular windows.

The ultraviolet transparent housing can have the ultraviolet light emitting source(s), the ultraviolet transparent optical element(s) and any other components (e.g., sensor(s)) disposed therewith in any of a number of configurations. For example, these components can be disposed about the housing in a number of locations that include, but are not limited to, on an internal wall of the housing, on an external wall of the housing, or suspended within the housing.

With any of the various embodiments, at least one sensor can be configured with the aforementioned components and deployed in an ultraviolet illuminator or ultraviolet illumination system, such that the sensor(s) can detect operational conditions associated with the irradiation of at least one object or fluid by the ultraviolet light emitting source(s). A number of different sensors can be used singly or in a multiple of combinations to detect operation conditions of the irradiation. The sensors can include, but are not limited to, a fluorescent sensor to detect the fluorescence emissivity of the object or fluid after irradiation by one or more ultraviolet light emitting sources, an ultraviolet radiation sensor to detect the ultraviolet intensity at the surface of an object or fluid that is being irradiated, a temperature sensor to detect the temperature about the ultraviolet transparent housing, a humidity sensor to detect the humidity within the housing, and a fluid transparency sensor to detect the transparency of a fluid that is undergoing irradiation, and a chemical sensor to detect chemical components in the fluid or at the surface of object that is being irradiated.

The various embodiments described herein can further include a control unit that is operatively coupled to the ultraviolet light emitting source(s) and the sensor(s) to control the irradiation of the object or the fluid. The operation of the ultraviolet light emitting source(s) and sensor(s) with the control unit enables the various embodiments to incorporate a feedback mechanism that facilitates monitoring the irradiation of the object or the fluid. For example, this feedback mechanism enables the control unit to determine a presence of harmful contaminants about the object or in the fluid based on the conditions detected by the sensor(s). This allows the control unit to direct the ultraviolet light emitting source(s) to irradiate the object or fluid at locations where there is a presence of harmful contaminants for removal and suppression thereof.

In addition, the control unit can monitor the irradiation of the object or fluid with feedback from the conditions detected by the sensor(s). As a result, the control unit can adjust the irradiation parameters of the ultraviolet light emitting source(s) as a function of conditions detected by the sensor(s). The irradiation parameters can comprise the wavelength of the ultraviolet radiation emitted by the ultraviolet light emitting source(s), an intensity or overall dosage of the ultraviolet radiation delivered to the object or fluid by the ultraviolet light emitting source(s), and a treatment time that the ultraviolet light emitting source(s) deliver the ultraviolet radiation. Other irradiation parameters can include, but are not limited to, a power setting for operating the ultraviolet light emitting source(s), and a maximum operating temperature of the ultraviolet light emitting source(s).

The sensor(s) and the control unit can be configured with the ultraviolet transparent housing having the ultraviolet light emitting source(s) and the ultraviolet transparent optical element(s) in one of a number of different approaches. For example, in one embodiment, the ultraviolet light emitting source(s) can be configured to stimulate a fluorescent response from an object or fluid, while a fluorescent sensor can be configured to detect the fluorescent response and generate a fluorescent signal representative of the intensity of the fluorescence generated from the object or fluid. The control unit can be configured to determine whether the intensity of the fluorescent signal detected by the fluorescent sensor is indicative of a contamination condition present on a surface of the object or in the water. To this extent, the control unit can activate one or more of the ultraviolet light emitting sources that are configured to operate as an UV-C light emitting source and/or an UV-A light emitting source to perform a disinfection operation on the object or fluid in response to determining the contamination condition.

In one embodiment, an ultraviolet radiation sensor can be configured to detect the ultraviolet intensity of fluid in an aquatic environment after being irradiated with ultraviolet radiation, while a fluorescent sensor can be configured to detect the fluorescent illumination intensity of the fluid after being irradiated by another ultraviolet radiation source. In this manner, a control unit can receive signals indicative of the conditions detected by the ultraviolet radiation sensor and the fluorescent sensor, and determine a fluid transparency of the fluid and an algae density level. If the control unit determines that the algae density level is too high (e.g., the algae density level satisfies a predetermined threshold), then it can activate the operation of the ultraviolet radiation source(s) to eradicate the algae. In addition, the control unit and the sensors can be configured to manage the irradiation of the fluid by monitoring conditions of the fluid during irradiation and adjusting the irradiation parameters of the ultraviolet radiation source(s) as a function of the detected ultraviolet intensity in the fluid and the detected fluorescent illumination intensity.

The control unit can include a number of different components that enable it to control the ultraviolet light emitting source(s) and make any determinations relating to the irradiation of the object or fluid based on data obtained from the sensor(s). For example, other components that may be utilized with the control unit can include a timer, an input component and an output component (e.g., an input/output component) and a power supply. The timer can be set in accordance with the specified treatment time in order to ensure that the ultraviolet light emitting source(s) deliver a sufficient dosage to the fluid and/or surfaces of the object. The input component can permit a user to adjust at least one of the above-noted irradiation parameters, and the output component can indicate status information of the irradiation of the fluid and/or surfaces of the object (e.g., on, off, treated, needs treatment, etc.), as well as generate information of more specific details of the treatment. The power supply can provide power to all of these components. These components are not limited to use with only the control unit, but can also be implemented as parts of an ultraviolet illuminator or an ultraviolet illumination system and used to operate in conjunction with the control unit, ultraviolet light emitting source(s) and the sensor(s).

The various embodiments can be further configured with other components that complement the irradiation of the object or fluid in order to further enhance the sterilization, disinfection, treatment, and the like, of these subjects. For example, the irradiation of an object or fluid can be enhanced by utilizing a visible light emitting source to irradiate these items with visible light. To this extent, the visible light emitting source can aid the ultraviolet light emitting source(s) in disinfecting any harmful contaminants from an object or fluid and suppressing further growth. In one embodiment, a photocatalyst material can be used with any of the various embodiments to facilitate the irradiation of an object or fluid. For example, the photocatalyst material can undergo a photocatalytic reaction in response to being irradiated by ultraviolet radiation. This photocatalytic reaction can facilitate the removal and suppression of any harmful contaminants present on the surface of an object or a fluid that is being irradiated by ultraviolet light emitting source(s).

A first aspect of the invention provides a system, comprising: at least one ultraviolet light emitting source having at least one light emitting side; an ultraviolet transparent housing that encapsulates the at least one ultraviolet light emitting source, the ultraviolet transparent housing including an ultraviolet transparent material that transmits ultraviolet light from the at least one ultraviolet light emitting source while preventing humidity from penetrating the ultraviolet transparent housing and damaging the at least one ultraviolet light emitting source; and at least one ultraviolet transparent optical element located about the ultraviolet transparent housing interspersed with the ultraviolet transparent material.

A second aspect of the invention provides a system, comprising: a set of ultraviolet light emitting sources each having at least one light emitting side to emit ultraviolet light, wherein at least one of the ultraviolet light emitting sources includes an ultraviolet-C (UV-C) light emitting source; an ultraviolet transparent housing having an ultraviolet transparent film that encapsulates the set of ultraviolet light emitting sources, the ultraviolet transparent film preventing humidity from penetrating the ultraviolet transparent housing and damaging the set of ultraviolet light emitting sources; and a set of ultraviolet transparent optical elements located about the ultraviolet transparent housing interspersed with the ultraviolet transparent film, the set of ultraviolet transparent optical elements including a primary set of optical elements and a secondary set of optical elements, wherein each of the primary set of optical elements is located at interface between the ultraviolet transparent film and one of the ultraviolet light emitting sources, and wherein each of the secondary set of optical elements is located about one of ultraviolet light emitting sources.

A third aspect of the invention provides a system, comprising: a set of ultraviolet light emitting sources each having at least one light emitting side to emit ultraviolet light, wherein the set of ultraviolet light emitting sources includes at least one ultraviolet-C (UV-C) light emitting source and at least one blue-ultraviolet (blue-UV) light emitting source; an ultraviolet transparent housing having an ultraviolet transparent material that encapsulates the set of ultraviolet light emitting sources, the ultraviolet transparent housing including an external surface to support at least one object for undergoing irradiation by the set of ultraviolet radiation sources; at least one ultraviolet transparent optical element located about the ultraviolet transparent housing interspersed with the ultraviolet transparent material to focus ultraviolet light onto a surface of the at least one object; at least one sensor configured to detect operational conditions associated with the irradiation of the at least one object by the set of ultraviolet light emitting sources; a control unit, operatively coupled to the set of ultraviolet light emitting sources and the at least one sensor to control the irradiation of the at least one object; and a user input/output component configured to facilitate user interaction with the control unit.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
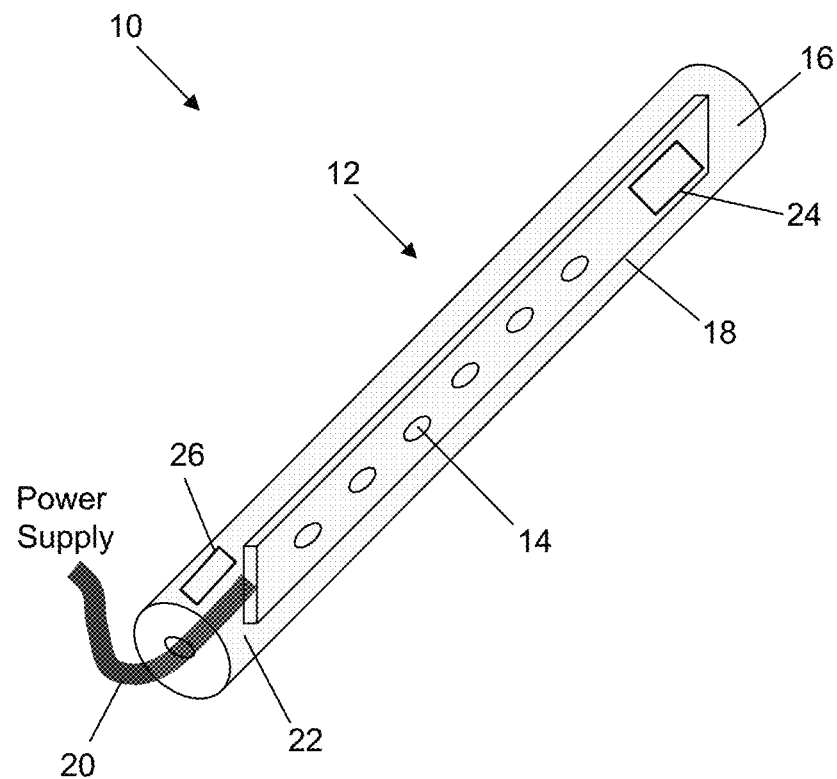
FIG. 1 shows a schematic of an ultraviolet illumination system having an ultraviolet illuminator with ultraviolet light emitting sources disposed in a cylinder-shaped ultraviolet transparent housing that can irradiate a subject such as an object or fluid according to an embodiment.

As indicated above, aspects of the invention are directed to solutions that use ultraviolet radiation with optical elements to irradiate objects and/or fluids for purposes of sterilization, disinfection, and/or cleaning these subjects of microorganisms, parasitic agents, bacteria, viruses, germs or other harmful contaminants. Ultraviolet irradiation of a surface of an object or a body or volume of fluid can entail sanitizing, disinfecting, and/or sterilizing. Sanitizing generally means reducing the number of bacterial contaminants to a predetermined safe level. Disinfecting generally means destroying pathogenic and other types of microorganisms, while sterilizing can be more extensive in that it kills all microbial forms and/or includes destroying the ability of the microbial forms to reproduce.

Ultraviolet radiation, which can be used interchangeably with ultraviolet light, means electromagnetic radiation generally described as having a wavelength ranging from approximately 10 nm to approximately 400 nm. Within this range, there is ultraviolet-A (UV-A) electromagnetic radiation generally described as having a wavelength ranging from approximately 310 nm to approximately 400 nm, ultraviolet-B (UV-B) electromagnetic radiation generally described as having a wavelength ranging from approximately 280 nm to approximately 360 nm, and ultraviolet-C (UV-C) electromagnetic radiation generally described as having a wavelength ranging from approximately 100 nm to approximately 280 nm. As used herein, blue-UV radiation includes at least a portion of the UV-A electromagnetic radiation as well as higher wavelength visible light, e.g., visible light having a wavelength ranging from approximately 400 nm to approximately 460 nm (380 nm to 420 nm in a more particular embodiment).

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 250 nm to 280 nm is a range for facilitating sterilization and disinfection of a vast amount of object and fluid that can develop the presence of contaminants. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The ultraviolet illuminators and ultraviolet illumination systems deploying such illuminators as described in the various embodiments can include a number of components. These components are described below in more detail, some of which may be optional, facilitate the treatment of objects and fluids. The modalities used with the various ultraviolet illuminators and irradiation systems described herein including its respective components can include any now known or later developed approaches that incorporate the concepts of the embodiments described below in more detail.

The description that follows may use other terminology herein for the purpose of only describing particular embodiments and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof. Additionally, spatially relative terms, such as "on," "below," "above," etc., may be used in reference to the orientation shown in the drawings. It is understood that embodiments of the invention are not limited to any particular orientation of a device described herein. Also, the use of a phrase of the form "at least one of A, B, C . . . or n" to delineate a listing of two or more possible parameters, components, characteristics, factors, etc., means any combination of one or more of A, B, C, n. For example, at least one of A or B means only A, only B, or both A and B.

The description may also list values of parameters of elements, components, materials, layers, structures, and the like, for the purpose of describing further details of particular embodiments. It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value. A value, y, is on the order of a stated value, x, when the value y satisfies the formula $0.1x \leq y \leq 10x$. Unless otherwise stated, as used herein, parameters can have comparable values when the values of the corresponding parameters differ by at most ten percent (five percent in a more specific embodiment).

Turning to the drawings, FIG. 1 shows a schematic of an ultraviolet illumination system 10 having an ultraviolet illuminator 12 with ultraviolet light emitting sources 14 disposed in a cylinder-shaped ultraviolet transparent housing 16 that can irradiate a subject such as an object or fluid for purposes of sterilization, disinfection, cleaning, and/or the like. Objects that are suitable for use with the ultraviolet illuminator 12 as well as any of the other illuminators described herein can include any item, article, or subject that is susceptible to the build-up of undesirable contaminants (e.g., microorganisms, parasitic agents, bacteria, viruses, germs, etc.) such as for example food, door handles, toilet seats, etc., while the illuminators are applicable for treating a wide variety of fluids or bodies of fluids (e.g., aquatic environments, pools, tanks, fluid dispensers, etc.) where it is desirable to suppress, remove and eliminate undesirable contaminants. To this extent, the ultraviolet illuminators can irradiate the objects or fluids with ultraviolet radiation to sterilize and/or disinfect the objects or fluids, while removing or eliminating contaminants and suppressing further growth.

As shown in FIG. 1, the ultraviolet illuminator 12 can include a set of ultraviolet light emitting sources 14 having at least one light emitting side to emit ultraviolet radiation.

In one embodiment, the ultraviolet light emitting sources 14 can be installed over an electrical component connecting board 18 such as a printed circuit board that is coupled to a power supply via a wired connection 20. The ultraviolet light emitting sources 14 along with the electrical component connecting board 18 can be encapsulated within the cylinder-shaped ultraviolet transparent housing 16 to protect these components from environmental factors such as humidity. For example, in one embodiment, the cylinder-shaped ultraviolet transparent housing 16 can include an ultraviolet transparent structure such as a protective sleeve that facilitates placement and removal of the ultraviolet light emitting sources 14 along with the electrical component connecting board 18 from an internal chamber 22 of the housing. In this manner, the ultraviolet material of the ultraviolet transparent housing 16 can encapsulate the ultraviolet light emitting sources 14 and the electrical component connecting board 18, thereby preventing humidity from penetrating the housing and damaging any of the components encapsulated in the housing that can be affected by humidity.

The ultraviolet illuminator 12 of FIG. 1 represents only one configuration of implementing an illumination system and those skilled in the art will appreciate that this illuminator as well as those other ultraviolet illuminators described herein can be configured to have other arrangements. For example, the ultraviolet illuminator 12 is shown in FIG. 1 with a set of ultraviolet light emitting sources 14, however, it is understood that the ultraviolet illuminator of this embodiment as well as any of the other embodiments described herein can utilize only one ultraviolet light emitting source. In one embodiment, the set of ultraviolet light emitting sources 14 can be encapsulated within the internal chamber 22 of the ultraviolet transparent housing 16 without the use of the electrical component connecting board 18. For example, the set of ultraviolet light emitting sources 14 can be affixed to an inner wall of the internal chamber 22 of the ultraviolet transparent housing 16 through an ultraviolet transparent material. In one embodiment, more than one electrical component connecting board 18 can be used to connect different sets of ultraviolet light emitting sources 14. For example, a first electrical component connecting board 18 can be used to couple a set of UV-C light emitting sources, while a second electrical component connecting board 18 can be used to couple a set of UV-A light emitting sources, enabling the ultraviolet illuminator with the capability to selectively choose between different modes of ultraviolet irradiation. In one embodiment, the set of ultraviolet light emitting sources 14 can be movable, such that the sources can be moved and oriented to direct ultraviolet radiation in a desired manner to effectuate a particular ultraviolet treatment of an object or fluid. For example, the ultraviolet light emitting sources 14 can be configured to moveable over a predetermined number of degrees of freedom to facilitate irradiation of desired locations about an object or body of fluid.

The set of ultraviolet light emitting sources 14 can comprise any combination of one or more ultraviolet radiation emitter. For example, the set of ultraviolet light emitting sources 14 can include a high intensity ultraviolet lamp (e.g., a high intensity mercury lamp), a discharge lamp, ultraviolet light emitting diodes (LEDs), super luminescent LEDs, laser diodes, and/or the like. In an embodiment, the set of ultraviolet light emitting sources can include a set of light emitting diodes manufactured with one or more layers of materials selected from the group-III nitride material system (e.g., $Al_xIn_yGa_{1-X-Y}N$, where $0 \leq x$, $y \leq 1$, and $x+y \leq 1$ and/or alloys thereof). Additionally, the set of ultraviolet light emitting sources 14 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like. In addition, optical elements including but not limited to, lenses, prismatic ultraviolet transparent elements, mirror elements (e.g., a parabolic mirror element, an omnidirectional mirror, a planar mirror and/or the like) can be deployed as a primary and/or secondary of optical elements for focusing the radiation in a particular pattern and/or direction from the sources.

It is understood that both UV-C and blue-UV light emitting sources are capable of producing a distributed intensity over an area at a certain distance from the sources, where distances can range from a few centimeters to several meters. As used herein, irradiation of a location defines a region that is impinged by radiation, wherein the intensity of radiation deposited at the boundary of the region is at most 10% of the intensity of light deposited at the center of the region. It is understood that the position of irradiated locations can be adjusted to result in separate locations, wherein "separate" means that the intensity of radiation between the locations is no larger than 10% of the intensity in the center of the locations. In addition, these locations of irradiation can be designed to have relatively uniform radiation, with radiation intensity varying through the location of no more than several times between any two points within the location.

In one embodiment, each of the UV-C light emitting sources can be configured to irradiate radiation at a specific wavelength selected from a range extending from 250 nm to 360 nm. In general, for adequate optimization of the irradiation that is provided by the ultraviolet light emitting sources 14, the wavelength range can be selected to be significantly narrower, depending on the type of microorganisms that are to be treated. For instance, the wavelength range can extend from 270 nm to 320 nm, and in some cases, depending on the optimization target, the range can extend from 280 nm to 300 nm, or from 260 nm to 280 nm. In one embodiment, the ultraviolet light emitting sources can have a peak wavelength that ranges from 270 nm to 300 nm. In another embodiment, the ultraviolet light emitting sources can have a peak wavelength of 295 nm with a full width half maximum of 10 nm.

In one embodiment, the blue-UV light emitting sources can operate at a wavelength that ranges from 380 nm to 420 nm. The blue-UV light emitting sources can comprise high intensity wide coverage sources that are capable of continuous operation in an efficient matter over a large stretch of time. In an embodiment, the blue-UV light emitting sources can operate continuously for a duration of several days.

The ultraviolet transparent housing 16, as noted above, can have all or portions formed from an ultraviolet transparent material. To this extent, the ultraviolet transparent material can emit the ultraviolet light generated from the ultraviolet light emitting sources 14 while preventing humidity from penetrating the ultraviolet transparent housing 16 and damaging the sources. In one embodiment, the ultraviolet transparent material can include an ultraviolet transparent fluoropolymer that encapsulates the set of ultraviolet light emitting sources 14 contained therein, as well as any other sources, sensors, or components that maybe additionally integrated in the housing 16. Ultraviolet transparent fluoropolymers that include, but are not limited to, fluorinated ethylene propylene (FEP), tetrafluoroethylene hexafluoropropylene vinylidene fluoride (THV), polytetrafluoroethylene (PTFE), Cytop®, and/or the like, are examples of ultraviolet transparent material that are suitable for use as the ultraviolet transparent housing 16 in this embodiment, as well as any of the other embodiments described herein. In embodiments in which the ultraviolet illuminator is used for treating fluids, it is understood that the ultraviolet transparent housing can include other ultraviolet transparent materials that are chemically inert to any interaction with the fluid and chemically stable to withstand exposure to the ultraviolet radiation generated from the ultraviolet light emitting sources 14.

In one embodiment, the ultraviolet transparent material can comprise an ultraviolet transparent film. For example, the ultraviolet transparent film can cover at least one light emitting side of the ultraviolet light emitting sources 14. However, it is understood that the ultraviolet transparent film can be formed about the ultraviolet transparent housing 16 at other locations. For example, the ultraviolet transparent film can be adjacent ultraviolet light emitting sources that are configured to emit radiation through a corresponding ultraviolet transparent window to facilitate transmissivity of any light that does not pass through the windows. In one scenario in which the ultraviolet light emitting sources 14 include an ultraviolet light emitting diode die, the ultraviolet transparent film can be placed adjacent to the surface of the die. The ultraviolet transparent film can comprise a thin fluoropolymer film including, but not limited to, EFEP, Cytop®, Teflon®, and/or the like. In an alternative embodiment such elements can comprise $SiO_2$, $Al_2O_3$, $CaF_2$, $MgF_2$, and/or the like.

The ultraviolet transparent material of the ultraviolet transparent housing 16 can also comprise a composite material formed from two or more materials. Examples of a composite material that are suitable for use with the ultraviolet transparent housing 16 can include, but are not limited to, any combination of two or more of the aforementioned ultraviolet transparent fluoropolymers. In one embodiment, the composite material can comprise a multilayered structure. Furthermore, the composite material can comprise a layer of a first material with one or more domains of another material embedded therein. In a more particular embodiment, the composite material can comprise a multilayered structure formed with at least one layer being an ultraviolet transparent fluoropolymer having biofouling properties. In one scenario, such a multilayered structure can be used as a structure that forms at least a partial enclosure to treat a body of fluid. For example, the multilayered structure of the housing can include a channel that is immersed in the body of fluid such that the fluid can flow in and out of, while a layer positioned above the channel can have at least one ultraviolet light emitting source to irradiate the fluid, and any other components that can facilitate the treatment such as at least one sensor to detect irradiation conditions and a control unit to control the treatment of the fluid.

The ultraviolet illuminator 12 of FIG. 1, as well as any of the other illuminators of the other embodiments can also include at least one sensor 24 to detect operational conditions associated with the irradiation of an object or fluid by the ultraviolet light emitting sources 14. The sensor 24 can be encapsulated within the internal chamber 22 of the ultraviolet transparent housing 16. For example, as shown in FIG. 1, the sensor 24 can be connected to the electrical component connecting board 18 along with the ultraviolet light emitting sources 14. Although FIG. 1, shows the ultraviolet illuminator 12 having only one sensor 24 it is understood that additional sensors can be utilized. Further, it is understood that the sensor 24 can be located apart from the ultraviolet light emitting sources 14.

The sensor(s) 24 deployed with the ultraviolet illuminator 12 can include any of a number of different types of sensors used singly or in a multiple of combinations to detect operation conditions associated with the irradiation of an object or a fluid. The sensors can include, but are not limited to, a fluorescent sensor (e.g., a fluorometer) to detect the fluorescence emissivity of the object or fluid after irradiation by the ultraviolet light emitting sources 14, an ultraviolet radiation sensor to detect the ultraviolet intensity at the surface of the object or fluid that is being irradiated, a temperature sensor to detect the temperature about the ultraviolet transparent housing 16, a humidity sensor to detect the humidity within the housing, a fluid transparency sensor to detect the transparency of a fluid that is undergoing irradiation, and a chemical sensor (e.g., a pH sensor, a chlorine sensor, an alkalinity sensor, a nitrate sensor, a salinity sensor, etc.) to detect chemical components in the fluid or at the surface of the object that. In one embodiment, the sensor 24 can include a visible camera configured to obtain images from any of a number of various locations about the surface of the object or the fluid. For example, the images can be used to compare images from these locations at different times in order to detect the presence of any contaminants.

A multitude of different types of sensors can be used with any of the various embodiments of the present invention. Other sensors that are suitable for use with any of the various embodiments can include, but are not limited to, environmental sensors such as a pressure sensor. These environmental type sensors can used to detect the level or amount of a particular process parameter that each is intended to measure and send signals thereof to a control unit. These sensors can be deployed along with the ultraviolet light emitting sources 14 in any desired configuration. For example, the sensors can be interspersed in the housing 16 with the ultraviolet light emitting sources 14 or separated from the housing.

The ultraviolet illuminator 12 of FIG. 1, as well as any of the other illuminators of the other embodiments can also include a control unit 26, operatively coupled to the set of ultraviolet light emitting sources 14 and the sensor(s) 24 to control the irradiation of the object or the fluid. The operation of the ultraviolet light emitting sources 14 and sensor(s) 24 with the control unit 26 enables the ultraviolet illuminator 12 to monitor the irradiation of the object or the fluid. For example, the control unit 26 can determine a presence of harmful contaminants about the object or in the fluid based on the conditions detected by the sensor(s) 24. To this extent, the control unit 26 can adjust the irradiation parameters of the ultraviolet light emitting sources 14 as a function of conditions detected by the sensor(s) 24. The irradiation parameters can comprise the wavelength of the ultraviolet radiation emitted by the ultraviolet light emitting sources 14, an intensity or overall dosage of the ultraviolet radiation delivered to the object or fluid by the ultraviolet light emitting sources, and a treatment time that the ultraviolet light emitting sources deliver the ultraviolet radiation. Other irradiation parameters can include, but are not limited to, a power setting for operating the ultraviolet light emitting sources 14, and a maximum operating temperature of the ultraviolet light emitting sources.

In one embodiment, the control unit 26 can activate the operation of the ultraviolet light emitting sources 14 in response to determining that there is a presence of an amount of contaminants about the surface of an object or in the fluid that exceeds a predetermined threshold, and thus, necessitating an ultraviolet treatment. Activating the operation of the ultraviolet light emitting sources 14 by the control unit 26 can include specifying any of the aforementioned irradiation parameters. It is understood that other irradiation parameters can be specified and/or adjusted. Other irradiation parameters can include, but are not limited to, the angular distribution of the ultraviolet radiation transmitted from the ultraviolet light emitting sources 14. It is understood that all of these irradiation parameters are illustrative of some of the parameters that can be set by the control unit and are not meant to be limiting as other parameters exist which may be specified.

The sensor(s) 24 and the control unit 26 can be configured to operate with the ultraviolet light emitting sources 14 in one of a number of different approaches. For example, in one embodiment, the ultraviolet light emitting sources 14 can be configured to stimulate a fluorescent response from an object or a fluid, while a sensor 24 such as a fluorescent sensor can be configured to detect the fluorescent response and generate a fluorescent signal representative of the intensity of the fluorescence generated from the object or fluid. The control unit 26 can be configured to determine whether the intensity of the fluorescent signal detected by the fluorescent sensor is indicative of a contamination condition present on a surface of the object or in the water. In this manner, the control unit 26 can activate one or more of the ultraviolet light emitting sources that are configured to operate as an UV-C light emitting source and/or an UV-A light emitting source to perform a disinfection operation on the object or fluid in response to determining the contamination condition.

In one embodiment, the ultraviolet illuminator 12 can include an ultraviolet radiation sensor configured to detect the ultraviolet intensity of fluid in an aquatic environment after being irradiated with ultraviolet radiation, while a fluorescent sensor can be configured to detect the fluorescent illumination intensity of the fluid after being irradiated by another ultraviolet radiation source. The control unit 26 can receive signals indicative of the conditions detected by the ultraviolet radiation sensor and the fluorescent sensor, and determine a fluid transparency of the fluid and an algae density level. If the control unit 26 determines that the algae density level is too high (e.g., the algae density level satisfies a predetermined threshold), then it can activate the operation of the ultraviolet light emitting sources 14 to eradicate the algae. In addition, the control unit 26 and the sensors can be configured to manage the irradiation of the fluid by monitoring conditions of the fluid during irradiation and adjusting the irradiation parameters of the ultraviolet light emitting sources 14 as a function of the detected ultraviolet intensity in the fluid and the detected fluorescent illumination intensity.

The control unit 26 can include a number of different components that enable it to control the ultraviolet light emitting sources 14 and make determinations relating to the irradiation of the object or fluid based on data obtained from the sensor(s) 24. For example, the control unit 26 can have a memory storage that is capable of recording the various data obtained from the sensors. To this extent, the control unit 26 can retrieve the data for further analysis and optimization of the irradiation parameters of the ultraviolet light emitting sources 14. The control unit 26 can further include a timer with switches and/or the like, which can be integrated with the control unit or as a separate component. To this extent, the timer can be used to manage the duration that the ultraviolet light emitting sources 14 are on for a particular ultraviolet treatment and ensure that radiation is applied for that duration. In one embodiment, the control unit 26 operating in conjunction with the timer can manage the amount of time that the ultraviolet light emitting sources 14 radiate in the UV-C range versus the UV-B range and/or UV-A range. The duration and frequency that the ultraviolet light emitting sources 14 are utilized can depend on detected condition signals provided to the control unit 26 by any of the sensor(s) 24.

In an embodiment, the control unit 26 can include an input component and an output component (e.g., an input/output component) that allows a user to interact with the system 10 and the ultraviolet illuminator 12. For example, the input component can permit the user to adjust at least one of the aforementioned irradiation parameters. This can include making adjustments during the ultraviolet irradiation treatment and/or prior to initiating a treatment. For example, a user can use the input component to adjust both the intensity and dosage of the ultraviolet radiation generated from the ultraviolet light emitting sources 14. In one embodiment, the input component can include a set of buttons and/or a touch screen to enable the user to specify various input selections regarding the irradiation parameters. The output component can include a number of different output devices to present information to the user such as, for example, a vibration device, a visible light (e.g., flashing), an auditory signal generated by a speaker, and/or the like. For example, the output component can include a visual display for providing status information on the ultraviolet irradiation of the object or fluid (e.g., time remaining, the presence of bacteria, viruses, germs, or the like) and the condition of the object or fluid (e.g., surface changes, fluid appearance changes, presence of contaminants). In addition, the output component can include a visual indicator that indicates whether an ultraviolet irradiation treatment is recommended, whether the object or fluid has been sterilized, disinfected, sanitized, whether an ultraviolet treatment is underway (e.g., an illuminated light), or whether the treatment is over (e.g., absence of an illuminated light).

Both the control unit 26 and the sensor(s) 24 can include a wireless transmitter and receiver that is configured to facilitate communications with each other at a remote location via WiFi, BLUETOOTH, and/or the like. As used herein, a remote location is a location that is apart from any of the irradiation systems described herein. For example, a remote computer can be used to transmit operational instructions to the wireless transmitter and receiver. The operational instructions can be used to program functions performed and managed by the control unit 26 and the sensor(s) 24. In another embodiment, the wireless transmitter and receiver can transmit ultraviolet treatment results, data from and to the remote computer, to facilitate maintenance and diagnostic operations on the irradiation systems.

The ultraviolet illuminator 12 of FIG. 1 as well as the illuminators of the other embodiments described herein can further include a power source that is configured to power each of the ultraviolet light emitting sources 14, the control unit 26 and the sensor(s) 24. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the ultraviolet illuminator 12 including the ultraviolet light emitting sources 14, the control unit 26 and the sensor(s) 24 can include a mechanical energy to electrical energy converter such as a piezoelectric crystal, and a rechargeable device.

The ultraviolet illuminator 12 of the various embodiments can also include a heat dissipating component. A heat dissipating component enables the electronic componentry associated with the ultraviolet light emitting sources 14, the control unit 26, the sensor(s) 24 and the power source to operate efficiently without overheating. Examples of a heat dissipating component can include, but are not limited to, a heat sink, an air fan, and/or other heat dissipating mechanisms, such as liquid heating.

Figure 2:
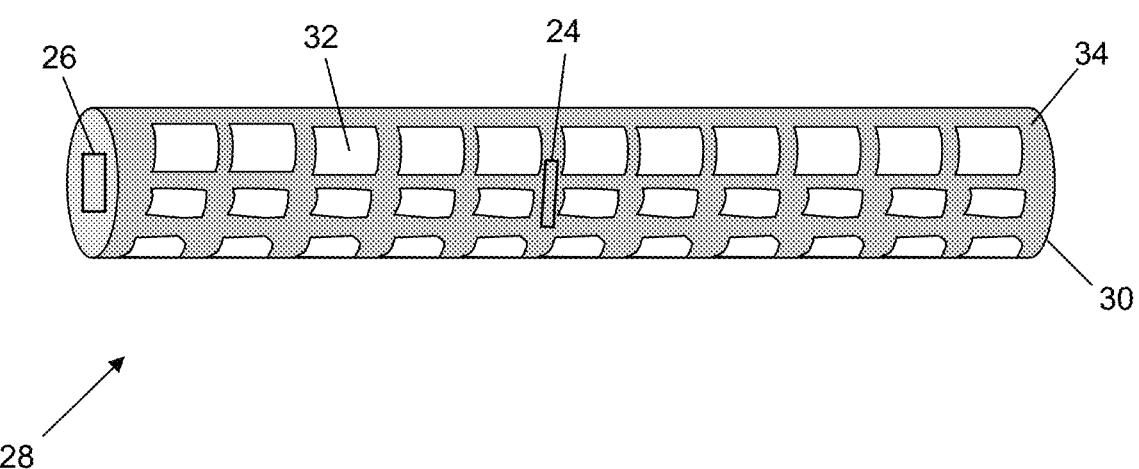
FIG. 2 shows a schematic of an ultraviolet illuminator having an ultraviolet transparent mesh housing having a plurality ultraviolet transparent windows integrated within an interlaced structure for transmitting ultraviolet light generated from ultraviolet light emitting sources disposed within the housing according to an embodiment.

FIG. 2 shows a schematic of an ultraviolet illuminator 28 having an ultraviolet transparent mesh housing 30 having a plurality ultraviolet transparent windows 32 integrated within an interlaced structure 34 for transmitting ultraviolet light generated from ultraviolet light emitting sources (not depicted) disposed within the housing. In one embodiment, each ultraviolet transparent window 32 can be configured to emit ultraviolet light there through, while the interlaced structure 34 can be configured to block any light from passing there through. In general, the interlaced structure 34 is a thicker material that provides structural support for the ultraviolet transparent mesh housing 30 so that it results in a non-collapsible structure, while the ultraviolet transparent windows 32 are a thinner, ultraviolet transparent material. The ultraviolet transparent windows 32 can cover more surface area of the housing 30 than the interlaced structure 34 in order to attain an overall structure that transmits ultraviolet radiation. It is understood that the ultraviolet transparent mesh housing 30 can have other designs such that the ultraviolet transparent windows 32 do not occupy as much surface area.

The ultraviolet transparent windows 32 and the interlaced structure 34 can be formed from one of a variety of materials. For example, the ultraviolet transparent windows 32 can comprise an ultraviolet transparent fluoropolymer that can transmit ultraviolet light and prevent the buildup of humidity within the housing 30. In one embodiment, ultraviolet transparent fluoropolymer that can be used for the ultraviolet transparent windows 32 is selected from the group consisting of EFEP, Cytop®, Teflon®, $SiO_2$, $Al_2O_3$, $CaF_2$, and $MgF_2$. It is understood that other ultraviolet transparent fluoropolymers can be used to form the ultraviolet transparent windows 32. The interlaced structure 34 can comprise a strong polymer or fluoropolymer that can transmit or block ultraviolet light and also prevent the buildup of humidity in the housing 30 such as, but not limited to, any suitable polymer or fluoropolymer described herein. It is understood that the interlaced structure 34 is not limited to a polymer or fluoropolymer and can be configured with other strong materials that can prevent the buildup of humidity within the structure.

As noted above, the ultraviolet light emitting sources of the ultraviolet illuminator 28 are not depicted in FIG. 2. It is understood that the ultraviolet light emitting sources can be encapsulated within the ultraviolet transparent mesh housing 30. Like the ultraviolet illuminator 10 of FIG. 1, the ultraviolet light emitting sources 14 can be encapsulated within the ultraviolet transparent mesh housing 30 via an electrical component connecting board 18. The encapsulation of the ultraviolet light emitting sources 14 with the electrical component connecting board 18 in the embodiments of FIGS. 1 and 2, as well as the other embodiments can be implemented in one of a variety of approaches. For example, the housing of the illuminators can encapsulate part of the electrical component connecting board 18 containing the ultraviolet light emitting sources 14 without completely enclosing the electrical component connecting board (e.g., a protective sleeve configuration). As noted above, the ultraviolet light emitting sources 14 can be encapsulated within the housing without using the electrical component connecting board 18. For example, the ultraviolet light emitting sources 14 can be encapsulated in a connected arrangement within the internal chamber of the housing. In another embodiment, the ultraviolet light emitting sources 14 can be mounted into a package that can contain ultraviolet transparent windows. In still another embodiment, the ultraviolet light emitting sources 14 can be mounted into a package that can be encapsulated by a thin fluoropolymer film. It is understood that for any of these embodiments, it is desirable that the ultraviolet light emitting sources 14 be encapsulated in a manner that ensures that humidity does not affect operation of sources and the packaging of the ultraviolet light emitting sources, including the operation of contacts to the sources.

The ultraviolet illuminator 28 of FIG. 2, like any of the other embodiments can include at least one sensor 24 to detect operational conditions associated with the irradiation of an object or a body of fluid, as well as a control unit 26, operatively coupled to the set of ultraviolet light emitting sources and the at least one sensor to control the irradiation. The type and number of sensors 24, as well as the operations performed by the control unit 26 can include any of the previously described approaches. The selection of the sensors and the operations performed by the ultraviolet illuminators will depend on a variety of factors including, but not limited to, the subject being irradiated, the environment in which these components are used, etc.

The ultraviolet illuminators of the various embodiments can further include at least one ultraviolet transparent optical element located about the housing of the illuminators that is interspersed with the ultraviolet transparent material of the housing. To this extent, the ultraviolet transparent optical element can aid in focusing ultraviolet light onto a surface of an object or in a body of fluid. The ultraviolet transparent optical element(s) can include a lens element. Examples of a lens element can include, but are not limited to, a Fresnel lens and a total internal reflection (TIR) lens. In one embodiment, ultraviolet transparent optical element(s) can be configured as a set of lens elements. These lens elements can be formed from a fluoropolymer material that includes, but is not limited to, $SiO_2$, $CaF_2$, $MgF_2$, or a fluoropolymer.

Figure 3:
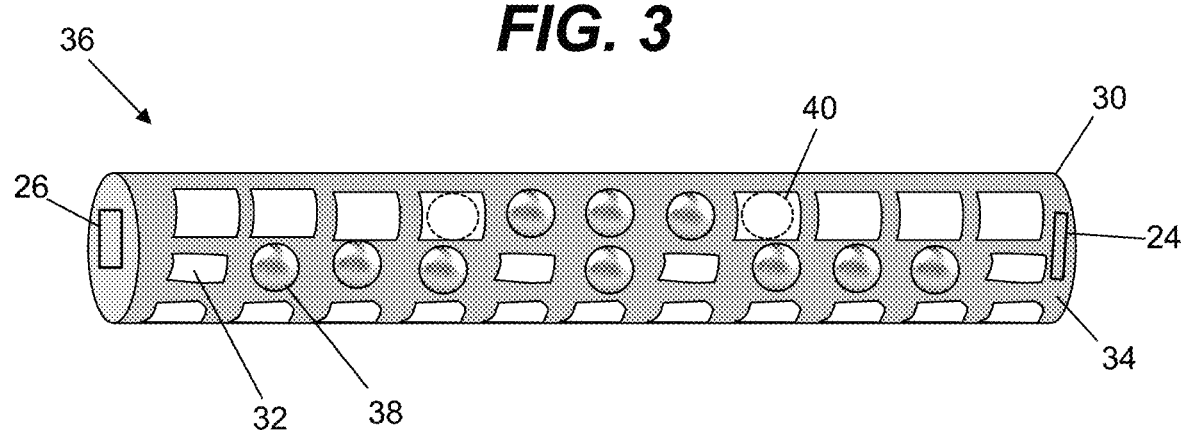
FIG. 3 shows a schematic of an ultraviolet illuminator having ultraviolet transparent optical elements disposed about an ultraviolet transparent mesh housing according to an embodiment.

FIG. 3 shows a schematic of an ultraviolet illuminator 36, similar to the illuminator 28 depicted in FIG. 2, except that the ultraviolet transparent mesh housing 30 in FIG. 3 includes a set of ultraviolet transparent optical elements 38 disposed within the interlaced structure 34 about the ultraviolet transparent windows 32. The set of ultraviolet transparent optical elements 38 can include, but are not limited to, a set of lens elements like Fresnel lenses and/or TIR lenses. In one embodiment, the Fresnel lenses can be formed from a fluoropolymer such as any of those previously mentioned. Further, the ultraviolet transparent optical elements 38 can be formed about the interlaced structure 34 in one of a variety of arrangements. For example, as shown in FIG. 3, the ultraviolet transparent optical elements 38 can be axially arranged about the cylinder-shaped housing 30 to provide optical element coverage along the length and/or the circumference of the housing. For example, in a scenario such as the one depicted in FIG. 3, the interlaced structure 34 can be formed from an ultraviolet transparent material that can transmit ultraviolet light from the housing 30 in addition to the light transmitted from the ultraviolet transparent windows 32. In this example, the ultraviolet transparent optical elements 38 can be positioned in the proximity or adjacent to an interface with the ultraviolet transparent material that is used with the interlaced structure 34.

It is understood that the number, the placement, and the type of ultraviolet transparent optical elements that are used with the housing of any of the ultraviolet illuminators can vary. For example, the illuminators can comprise a primary set of optical elements and a secondary set of optical elements that include any of the aforementioned lens elements. FIG. 3 illustrates an example of one scenario in which a primary set of optical elements and a secondary set of optical elements are used. As shown in FIG. 3, a primary set of optical elements 40 can be located at an interface between the ultraviolet transparent material of the housing where the ultraviolet transparent windows 32 are situated and the ultraviolet light emitting source(s) which could be positioned in an internal chamber underneath the windows. The set of optical elements 38 located about (i.e., next to, adjacent to, in the proximity to, but not over) the ultraviolet transparent windows 32 can be considered the secondary optical elements. In one embodiment, the primary set of optical elements can be encapsulated within the ultraviolet transparent housing 30 with the ultraviolet light emitting source(s) 14, while the secondary set of optical elements can be formed on the exterior of the housing (e.g., at an interface with the ultraviolet transparent material of the housing). In this manner, each of the primary and secondary optical elements can be optically coupled with the ultraviolet light emitting sources.

Figure 4:
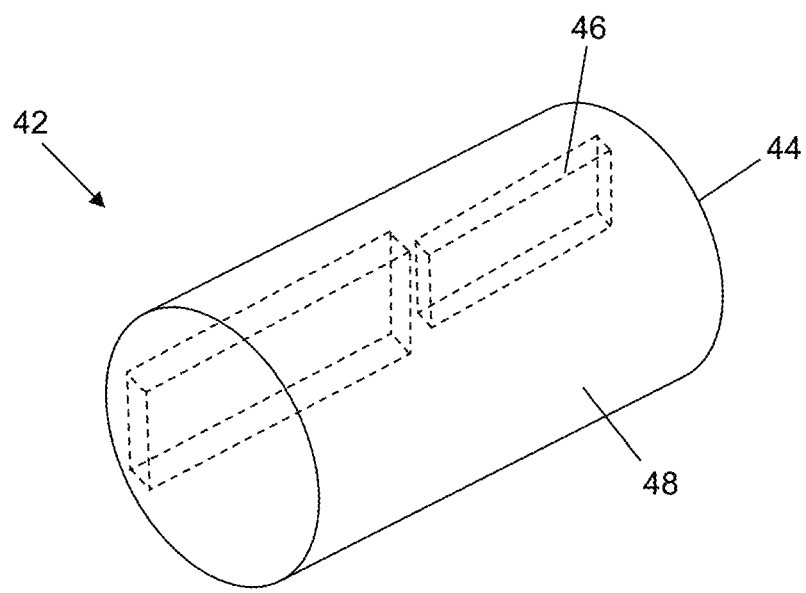
FIG. 4 shows a schematic of an ultraviolet illuminator having an ultraviolet transparent housing with a set of reflective elements positioned within an interior portion of the housing to provide structural support according to an embodiment.

FIG. 4 shows a schematic of an ultraviolet illuminator 42 having an ultraviolet transparent housing 44 with a set of reflective elements 46 positioned within an interior portion 48 of the housing to provide structural support according to an embodiment. The set of reflective elements can include, but are not limited to, polished aluminum, PTFE (e.g., Teflon®), expanding polytetrafluoroethylene (ePTFE), ETFE or combinations thereof. In another embodiment, a reflective element 46 can include a diffusive ultraviolet reflective surface. The diffusive ultraviolet reflective surface can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like. Each of the reflective elements 46 can be positioned in the interior portion 48 of the ultraviolet transparent housing 44 such that the reflective elements ensure that the housing does not collapse if a mechanical force were to be applied that could result in a structural deformation of the housing. For example, as shown in FIG. 4, the reflective elements 46 can positioned along the axial length of the housing. It is understood that the number and the location of the reflective elements 46 and the types of elements that are used will depend on a multitude of factors that can include the shape of the ultraviolet transparent housing 44, the items to be irradiated by the illuminators, and the type of irradiation treatment that is to be applied.

Figure 5:
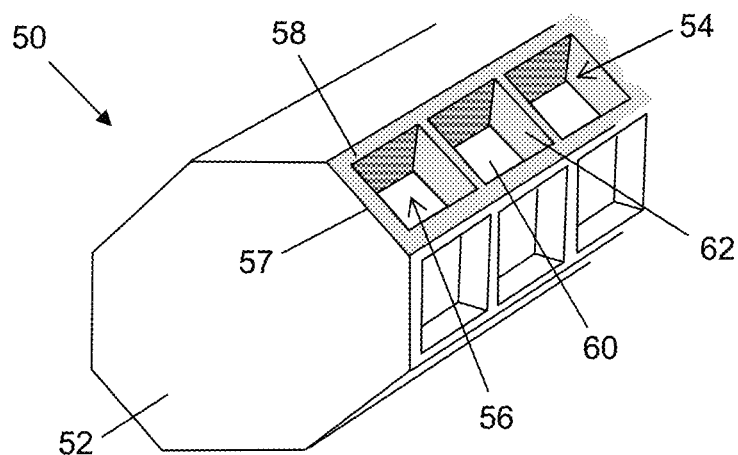
FIG. 5 shows a schematic of an ultraviolet illuminator having a cylinder-shaped ultraviolet transparent housing with cells formed from ultraviolet transparent cellular windows sunken in depressions located along an exterior surface of the housing according to an embodiment.

Structural support of the ultraviolet transparent housings of any of the ultraviolet illuminators can be obtained by other approaches that do not rely on internally positioned reflective elements such as that depicted in FIG. 4. For example, FIG. 5 shows a schematic of an ultraviolet illuminator 50 having a hexagonal cylinder-shaped ultraviolet transparent housing 52 with cells 54 formed from ultraviolet transparent cellular windows 56 sunken in depressions or voids 57 located along an exterior surface 58 of the housing according to an embodiment. Each of the ultraviolet transparent cellular windows 56 can have an ultraviolet transparent media 60 enclosed by supporting walls 62 that extend from the sunken depression 57 to the external surface area 58 of the ultraviolet transparent housing 52 to form ultraviolet transparent domains. The ultraviolet transparent media 60 of the ultraviolet transparent domains can include any of the aforementioned ultraviolet transparent fluoropolymers such as EFEP, Cytop®, Teflon®, $SiO_2$, $Al_2O_3$, $CaF_2$, $MgF_2$, and sapphire. While the cells 54 are shown having a rectangular cross-section and are shown as being arranged in rows, it is understood that alternative shapes and/or arrangements can be utilized. For example, the cells 54 can have hexagonal cross-sections with an hexagonal arrangement, thereby forming a hexagonal bee-hive type cell configuration, similar to a honeycomb of a bee-hive.

The supporting walls 62 of the ultraviolet transparent cellular windows 56 in the ultraviolet transparent domains can be configured to have low obstruction to the emitted ultraviolet light. The supporting walls 62 of the ultraviolet transparent cellular windows 56 can have small cross-sectional areas at least at one side of the cell walls. In one embodiment, at least one of the supporting walls 62 can have a reflective surface that is reflective to ultraviolet light to facilitate and/or improve ultraviolet transmission through the ultraviolet transparent cellular window 56 as well to promote recycling and light guiding of the radiation. For example, the reflective surface can be located at a lower portion of the supporting walls 62 adjoining the ultraviolet transparent cellular window 56. However, it is understood that all of the supporting walls 62 can include a reflective surface. The reflective surface can include a layer, film or coating of ultraviolet reflective material. In general, a layer, film or coating of ultraviolet reflective material with a reflection coefficient of at least 50% will enable recycling of the ultraviolet radiation generated from the ultraviolet light emitting sources.

Examples of ultraviolet reflective material that are suitable for use as a layer, film or coating can include, but are not limited to, polished aluminum, Bragg reflective dielectric mirrors, omni-directional mirrors comprising dielectric and metallic layers (e.g., aluminum), and/or the like. In one embodiment, the ultraviolet reflective material can include a diffusive ultraviolet reflective material such as a fluoropolymer. Examples of a fluoropolymer that are suitable as a diffusive ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

The ultraviolet transparent domains formed from the ultraviolet transparent cellular windows 56 create a set of structural elements that provide structural support of the cylinder-shaped ultraviolet transparent housing 52 to prevent a change in shape of the housing. The ultraviolet transparent domains can extend axially along the length of the ultraviolet transparent housing 52. These ultraviolet transparent domains can be positioned along all external surface area portions of the ultraviolet transparent housing 52 or along only limited portions. In one embodiment, the ultraviolet transparent domains can occupy at least 50% of the external surface area 58 of the ultraviolet transparent housing 52. As shown in FIG. 5, the regions between the cellular ultraviolet transparent windows 56 can have a small cross-sectional area, which along with the three-dimensional nature of the cells due to the clear depth and placement of the ultraviolet transparent media 60 provides structural stability for the ultraviolet transparent housing 52. In one embodiment, the regions between the cellular ultraviolet transparent windows 56 can have a characteristic size dimension that is about $\frac{1}{10}^{th}$ of the characteristic size dimension of the cellular ultraviolet transparent windows 56.

Although not shown in FIG. 5, the ultraviolet transparent domains of the ultraviolet transparent housing 52 formed from the ultraviolet transparent cellular windows 56 can have ultraviolet transparent optical elements formed there over. In this manner, the set of ultraviolet transparent domains and the ultraviolet transparent optical elements can operate cooperatively to focus ultraviolet light onto a surface of an object or at a fluid. With this configuration, the set of ultraviolet transparent domains and the ultraviolet transparent optical elements can illuminate the object or fluid with relatively uniform illumination. As used herein, relatively uniform illumination means that the uniformity of illumination is at least 30%. In one embodiment, some of the ultraviolet transparent domains can have an ultraviolet transparent optical element such as a lens formed there over, while others of the domains can be configured without an optical element.

The ultraviolet transparent domains can be formed with one of a variety of different materials. The types of material that can be used for the ultraviolet transparent domains can include, but are not limited to, any of the ultraviolet transparent materials discussed herein. In one embodiment, the ultraviolet transparent domains can be formed from more than one type of material (e.g., a composite material as described herein).

In one embodiment, the set of ultraviolet transparent domains can be optically connected by ultraviolet transparent wave guiding material that waveguides the ultraviolet light emitted from the ultraviolet light emitting sources along the ultraviolet transparent housing before emitting the radiation to an object or a body of fluid. As used herein, ultraviolet transparent wave guiding material means a transparent material that is configured to guide ultraviolet light therein for transmission at one or more predetermined locations. In one scenario, the ultraviolet transparent wave guiding material can include a plurality of light scattering elements from which the ultraviolet radiation is transmitted, however, other ultraviolet transparent wave guiding material can be used, such as for example, ultraviolet fiber, a diffusive ultraviolet emitter, and/or the like.

Figure 6:
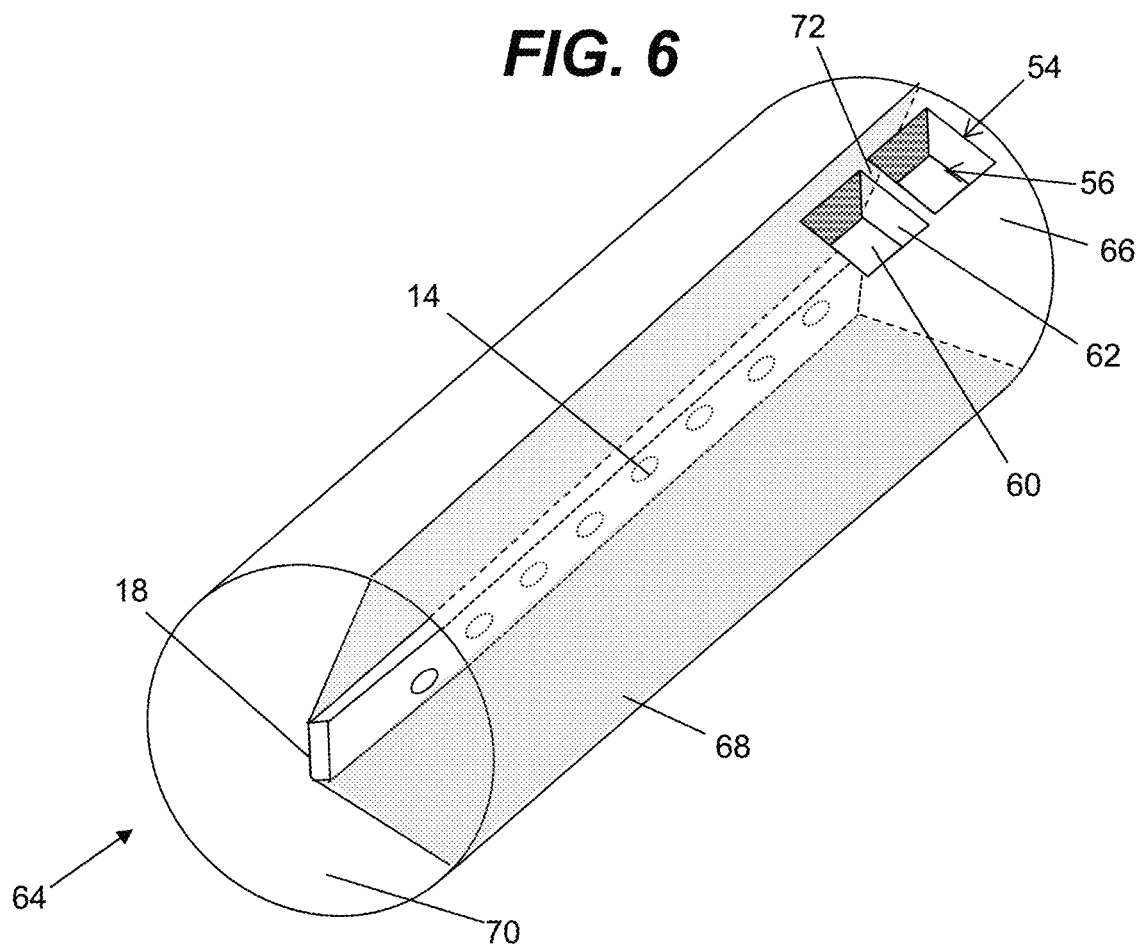
FIG. 6 shows a schematic of an ultraviolet illuminator having a cylinder-shaped ultraviolet transparent housing with a reflective element formed within an interior portion of the housing to direct ultraviolet light from ultraviolet light emitting sources to the ultraviolet transparent cellular windows located along an exterior surface of the housing according to an embodiment.

FIG. 6 shows a schematic of an ultraviolet illuminator 64 having a cylinder-shaped ultraviolet transparent housing 66 with a reflective element 68 formed within an interior portion 70 of the housing to direct ultraviolet light from ultraviolet light emitting sources 14 to the cells 54 formed from the ultraviolet transparent cellular windows 56 located along an exterior surface 72 of the housing according to an embodiment. The reflective element 68 can facilitate recycling of the ultraviolet radiation emitted from the ultraviolet light emitting sources 14 as well as improve transmission of the radiation through the ultraviolet transparent cellular windows 56. The reflective element 68 can include, but is not limited to, mirror elements, polished aluminum, and/or the like. In addition, the reflective element 68 can take on a variety of shapes which can depend on the cross-sectional shape of the internal portion of the housing as well as other factors that can include the intended use of the ultraviolet illuminator. In one embodiment, as shown in FIG. 6, the reflective element 68 can comprise a cone-shaped element formed about the electrical component connecting board 18 that optically couples the ultraviolet light emitting sources 14 to the ultraviolet transparent cellular windows 56. Although FIG. 6, shows that the reflective element 68 includes a single unitary element, it is understood that the reflective element can be configured from a multiple of reflective elements that can be similar elements, different elements, or combinations of different reflective elements. Further, it is understood that the reflective element 68 does not necessarily have to be formed about the electrical component connecting board 18 as shown in FIG. 6. Instead, the reflective element 68 can be positioned about the interior portion 70 of the ultraviolet transparent housing 66 in a different position and orientation all of which will depend on the positioning and encapsulation of the ultraviolet light emitting sources 14 in the housing, as well as other factors such as the type of ultraviolet illuminator and its intended use.

Figure 7:
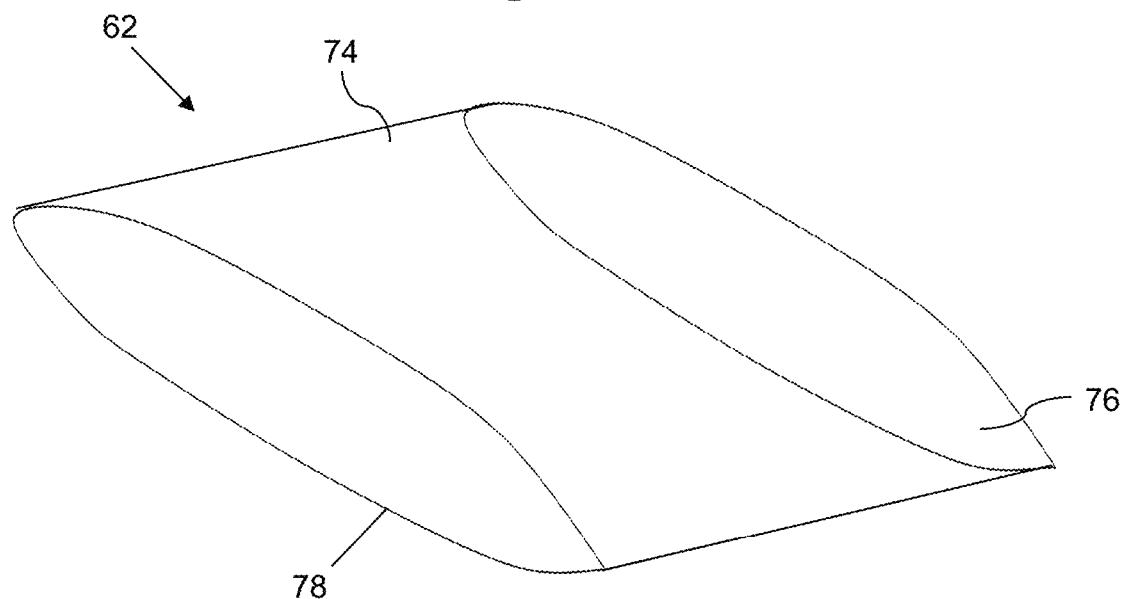
FIG. 7 shows a schematic of a more detailed view of one of the walls that can adjoin with other walls to form the ultraviolet transparent cellular windows depicted in the ultraviolet illuminators of FIGS. 5, and 6 according to an embodiment.

As noted above, the ultraviolet transparent media 60 and the supporting walls 62 of the ultraviolet transparent cellular windows 56 associated with the cells 54 that can be used with some of the ultraviolet transparent housings disclosed herein, can be configured to have low obstruction to the emitted ultraviolet light. FIG. 7 shows a schematic of a more detailed view of a typical supporting wall 62 that can adjoin with other walls to enclose the ultraviolet transparent media 60 to form an ultraviolet transparent cellular window depicted in the ultraviolet illuminators of FIGS. 5 and 6. As shown in FIG. 7, the supporting wall can include a back-tapering portion 74, a front-tapering portion 76, and an ultraviolet reflective surface portion 78. The back-tapering portion 74 and the front-tapering portion 76 make the supporting wall 62 structurally stable and result in the cells having low obstruction to light emitted from the ultraviolet light emitting sources. The ultraviolet reflective surface portion 78 of the supporting wall 62 can be located at a lower portion of the cells cellular window 56 to improve transmission and light guiding of the emitted light. It is understood that the supporting wall 62 can be configured according to other designs that have low obstruction to the emitted light, and the various embodiments are not meant to be limited to the approach depicted in FIG. 7.

Figure 8:
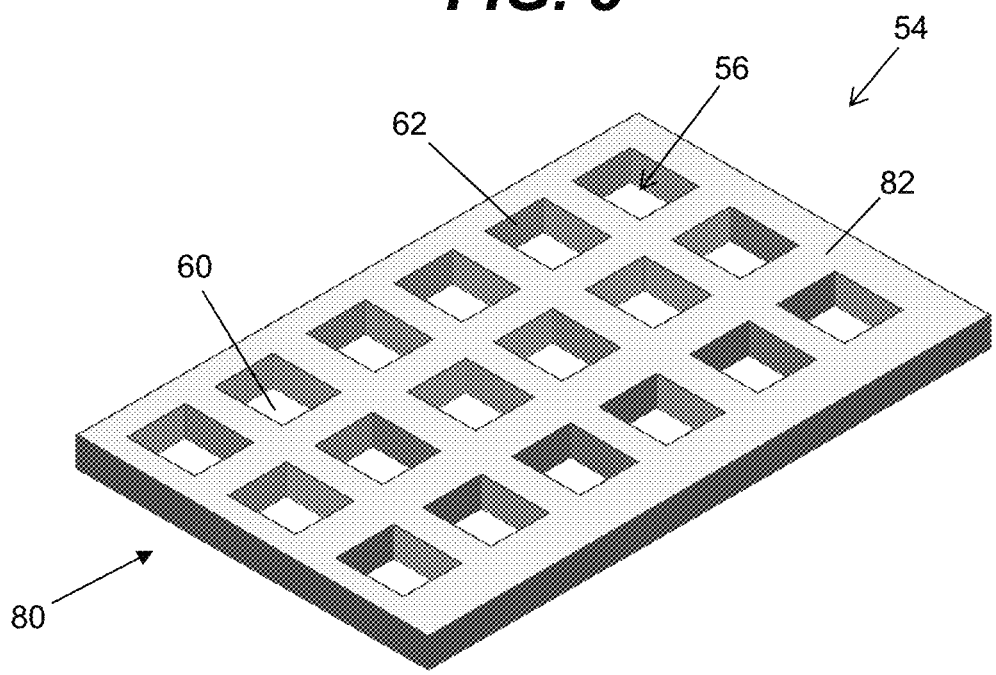
FIG. 8 shows a schematic of an ultraviolet illuminator with the cells formed in a flat, non-rounded ultraviolet transparent housing according to an embodiment.

The cells 54 of the ultraviolet transparent cellular windows 56 can be implemented with any of a variety of different-shaped ultraviolet transparent housing and are not meant to be limited to housing that are rounded or cylinder-shape. For example, FIG. 8 shows a schematic of an ultraviolet illuminator 80 with the cells 54 having the ultraviolet transparent cellular windows 56 formed in a flat, non-rounded ultraviolet transparent housing 82. The flat, non-rounded ultraviolet transparent housing 82 provides a structural element aspect to the housing that makes it and the accompanying components of an ultraviolet illuminator well situated for a variety of irradiation applications with regard to treating objects and bodies of fluid.

Figure 9:
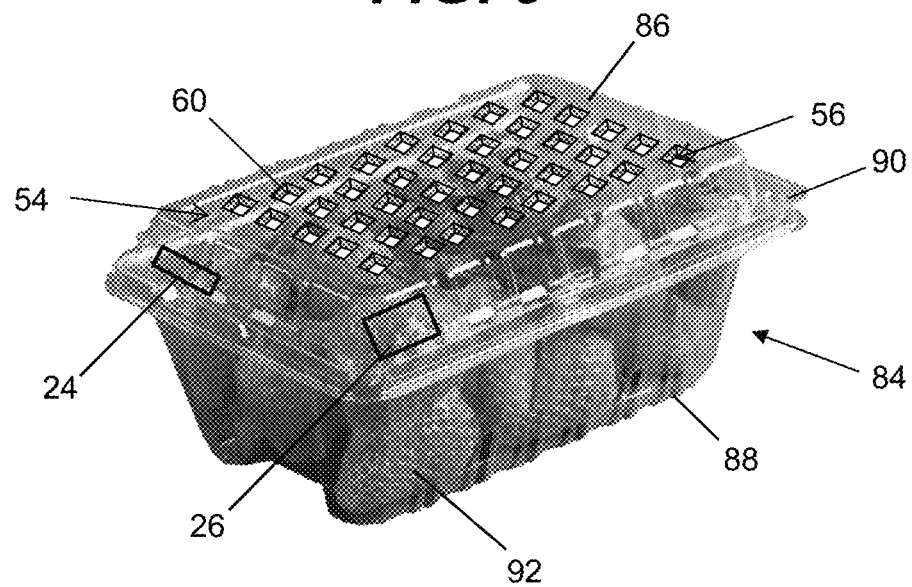
FIG. 9 shows a schematic of an ultraviolet illumination system with an ultraviolet illuminator having a flat, non-rounded ultraviolet transparent housing such as the one depicted in FIG. 8 implemented with a food container to irradiate food stored in the container according to an embodiment.

FIG. 9 shows a schematic of an ultraviolet illuminator 84 having a flat, non-rounded ultraviolet transparent housing 86 such as the one depicted in FIG. 6 implemented in a food container 88 to irradiate food stored in the container. In the embodiment depicted in FIG. 9, the ultraviolet transparent housing 86 can be arranged in the cover portion 90 of the food container 88. For example, in one scenario, although not expressly illustrated in FIG. 9, the ultraviolet light emitting sources 14 of the ultraviolet illuminator 84 can be positioned at location that is adjacent to the top section of the cover portion 90 of the food container 88 while the cells 54 with the ultraviolet transparent cellular windows 56 can be positioned at location that is adjacent to the bottom section of the cover in order to transmit light from the sources to the articles of food (e.g., strawberries) 92 that can be stored in the container. Although not shown in FIG. 9, one or more ultraviolet transparent optical elements can be arranged about the ultraviolet light emitting sources and/or about the irradiating side of the flat, non-rounded ultraviolet transparent housing 86 to focus the emitted light at the articles of food 92 in at least one of a predetermined pattern, direction, or angular distribution. The control unit 26 can control the irradiation of the articles of food 92 by the ultraviolet light emitting sources 14 as a function of data obtained by the at least one sensor 24 in accordance with any of the previously described approaches.

Figure 10:
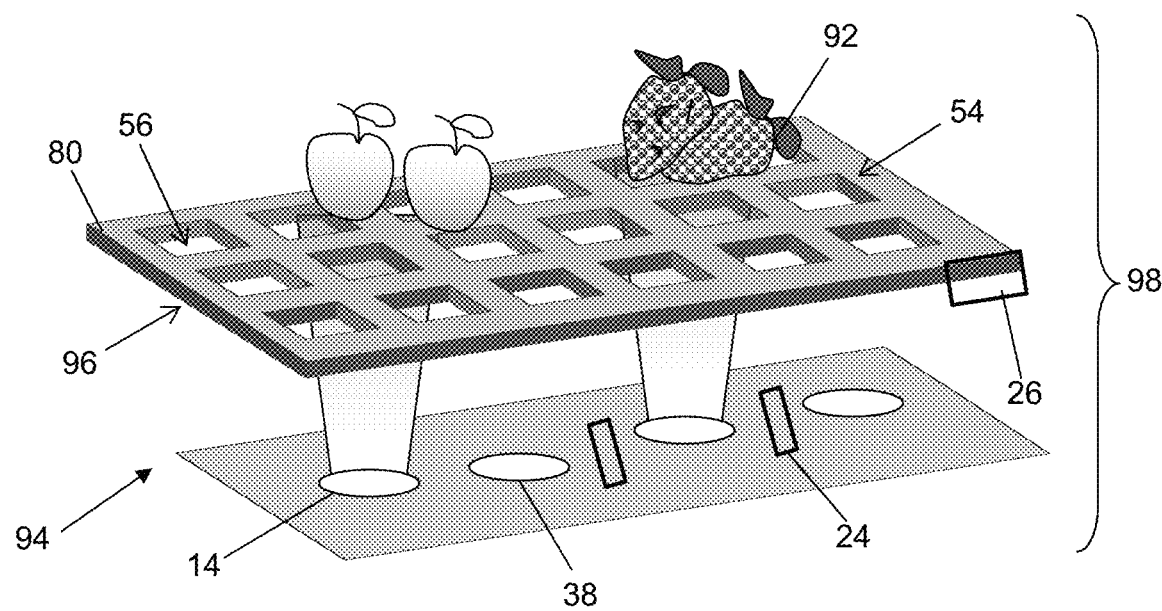
FIG. 10 shows a schematic of an ultraviolet illuminator having a flat, non-rounded ultraviolet transparent housing such as the one depicted in FIG. 8 implemented as a shelf within an ultraviolet illumination system for irradiating food placed on top of the shelf according to an embodiment.

In another example, FIG. 10 illustrates a schematic of an ultraviolet illuminator 94 having a flat, non-rounded ultraviolet transparent housing 80 such as the one depicted in FIG. 8 implemented as a shelf 96 within an irradiation system 98 for irradiating articles of food 92 (e.g., strawberries, apples, etc.) placed on top of the shelf. In the embodiment depicted in FIG. 10, the shelf 96 formed from the flat, non-rounded ultraviolet transparent housing 80 of the ultraviolet illuminator 94 can be implemented as part of a shelving unit within a refrigerator that supports articles and containers of food and the like, or as a kitchen accessory apart from the refrigerator that is used to perform similar functions. It is understood that the ultraviolet illuminator 94 including the flat, non-rounded ultraviolet transparent housing 80, the ultraviolet light emitting sources 14, the ultraviolet transparent optical elements 38 and other components (e.g., sensor 24 and control unit 26) can be utilized in a variety of settings in which it is desirable to disinfect objects that are subject to the proliferation of harmful microorganisms, contaminants, and the like. For example, the ultraviolet illuminator 94 can be used in a bathroom for example in the shower or in a medicine cabinet to disinfect items that can include, but are not limited to, toothbrushes, shavers, razors, brush, soaps, containers, and the like.

In one embodiment, as depicted in FIG. 10, the shelf 96 formed from the ultraviolet transparent housing 80 can be separated apart from the ultraviolet light emitting sources 14 and the ultraviolet transparent optical elements 38 at predetermined distance. In this manner, the cells 54 with the ultraviolet transparent cellular windows 56 and items supported thereon can be separated at predetermined distance apart from the ultraviolet light emitting sources 14. This allows the ultraviolet light emitting sources 14 to have the capability to emit different patterns and directions of light, as well as to emit the light at the articles of food 92 with a predetermined angular distribution.

Like other embodiments described herein, the control unit 26 can control the irradiation of the articles of food 92 by the ultraviolet light emitting sources 14 as a function of data obtained by the sensors 24 in accordance with any one of the previously described approaches. For example, the control unit 26 can direct the ultraviolet light emitting sources 14 to irradiate the articles of food 92 with multiple wavelengths such as UV-A, UV—B and/or UV-C radiation. In addition, the control unit 26 can monitor the irradiation based on feedback data provided by the sensors 24 and adjust any of the irradiation parameters of the ultraviolet light emitting sources 14 that can include, but are not limited to, changing the wavelength of the ultraviolet radiation emitted by the ultraviolet light emitting sources, the intensity or overall dosage of the sources as a function of time, the time that the ultraviolet light emitting sources deliver ultraviolet radiation, the power setting for operating the ultraviolet light emitting sources, and the maximum operating temperature of the ultraviolet light emitting sources.

It is understood that the ultraviolet illuminator 94 depicted in FIG. 10 represents only one possible arrangement of its accompanying components and is not meant to be limiting. For example, at least some or all of the ultraviolet transparent cellular windows 56 can have ultraviolet transparent optical elements formed therein. Similarly, at least some or all of the ultraviolet light emitting sources 14 can have ultraviolet transparent optical elements formed there over. In one embodiment, at least one of the ultraviolet light emitting sources 14 can be configured to be movable such that the emitted beams of light can be movable over a predetermined range of movement.

The flat, non-rounded ultraviolet transparent housing structures used in the ultraviolet illuminators of FIGS. 9-10 differ from the housings of the rounded ultraviolet transparent housings in that the structures of FIGS. 9-10 support objects in container and shelf arrangements, as well as transmit light to the objects within the container or on the shelf, and do not directly surround the ultraviolet light emitting sources that are a part of an ultraviolet illuminator. In both scenarios depicted in FIGS. 9-10, it is desirable to have the flat, non-rounded ultraviolet transparent housing structures comprise a mechanically strong and stable structure to support a considerable amount of weight. For example, the flat, non-rounded ultraviolet transparent housing 86 that is used to irradiate articles of food 92 such as strawberries stored in the food container 88 in FIG. 9 has to be movable and capable of withstanding a pressure due to other containers, items, and the like being placed on top of it. In particular, the flat, non-rounded ultraviolet transparent housing 86 should be able to withstand other food containers 88 placed over it. In addition, the flat, non-rounded ultraviolet transparent housing 86 should be able support the items stored in the container or on the shelf. For example, in the embodiment depicted in FIG. 9, the flat, non-rounded ultraviolet transparent housing 86 implemented in the food container 88 storing strawberries should have the structural stability that is capable of holding a load of at least one pound. With regard to the shelf 96 formed from the ultraviolet transparent housing 80 that is depicted in FIG. 10, it is desirable to have the shelf maintain its shape while holding relatively heavy objects that may require disinfection. In one embodiment, beyond a typical food or toiletry item storage application, the shelf 96 can be configured to maintain tens or even hundreds of pounds before collapsing and undergoing deformation.

Figure 11A:
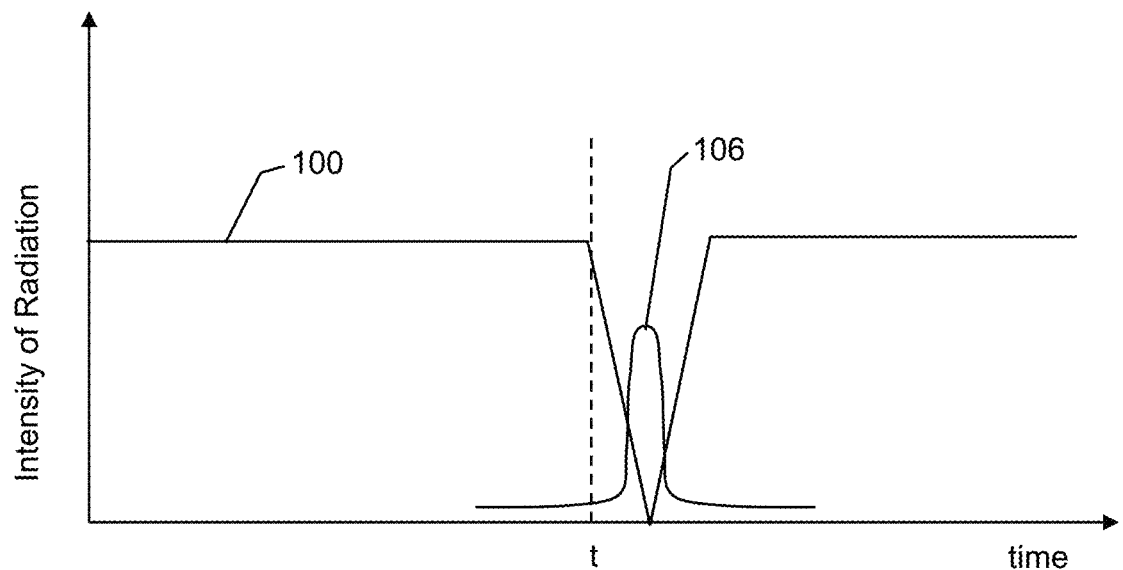
FIGS. 11A-11B show graphical examples depicting the operation of an ultraviolet illuminator according to an embodiment in which a first set of ultraviolet light emitting sources and a second set of ultraviolet light emitting sources are used to apply an ultraviolet irradiation treatment.
Figure 11B:
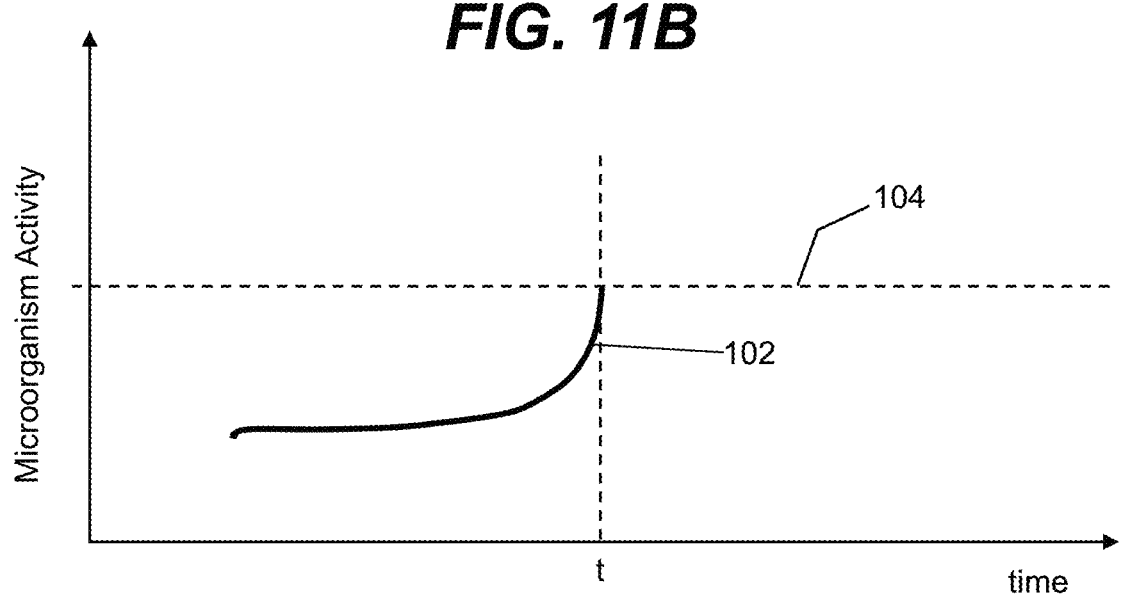

The various ultraviolet illuminators and ultraviolet illumination systems that utilize such illuminators as described herein can be operated in a variety of manners to deliver an irradiation treatment to an object or body of fluid. FIGS. 11A-11B show graphical examples depicting the operation of an ultraviolet illuminator that utilizes a first set of ultraviolet light emitting sources and a second set of ultraviolet light emitting sources.

As shown in FIG. 11A, at section 100 of the graph, ultraviolet radiation from a set of light emitting sources that emit light such as blue-UV radiation can be used to determine whether there is any contamination of the object or in the fluid based on data from a sensor (e.g., an amplitude of a fluorescent signal sensed by a fluorescent sensor, visual data from a visual camera, and/or the like). For example, the object or the body of fluid can be irradiated with a light emitting source that is capable of eliciting a fluorescent signal if microbial activity is present. The amplitude of the fluorescent signal can indicate the level of contamination and/or the amount of microbial activity. The object or fluid can be irradiated by blue-UV radiation over a prolonged period of time that ranges from tens of minutes to tens of hours while determining whether there is a fluorescent signal. During this time, the control unit and the sensor (e.g., the fluorescence sensor, visual camera, and the like) can operate in conjunction to monitor the amount of contamination present on the surface of the object or in the fluid.

In this example, FIG. 11B shows a sharp increase in the growth of microorganism activity as noted by reference element 102. When the level of microorganism activity approaches a predetermined contamination threshold 104 at time t that is indicative of a need for more intense ultraviolet irradiation treatment due to rapid growth of microbial activity, then the control unit can direct a set of ultraviolet light emitting sources that can emit UV-C radiation to perform a more intense ultraviolet irradiation treatment at a short burst of intensity that lasts at most a few minutes (FIG. 11A, reference number 106) starting at or shortly after time t. In this manner, ultraviolet radiation (e.g., UV-C radiation) applied from the set of ultraviolet light sources that deliver UV-C radiation can bring microbial activity within appropriate limits by rapidly suppressing microbial activity on the surface of the object. The blue-UV radiation from the set of light emitting sources that generate this type of radiation can be used to maintain microbial activity within limits over an extended period of time, while the UV-C radiation from the ultraviolet light sources that deliver UV-C radiation can be used to rapidly suppress microbial activity.

It is understood that the various ultraviolet illuminators and ultraviolet illumination systems described herein can include other components that can complement the irradiation of an object or fluid in order to further enhance the sterilization, disinfection, treatment, and the like, of these items. For example, the ultraviolet illuminators can utilize other sources to irradiate the items such as at least one visible light emitting source that emits visible light. To this extent, the visible light emitting source(s) can aid the ultraviolet light emitting source(s) in disinfecting any harmful contaminants from an object or fluid and suppressing further growth of these contaminants. Examples of visible light sources that can be used include, but are not limited to, visible light emitting diodes, fluorescent lights, compact fluorescent lights, neon lights, incandescent lights, etc. In one embodiment, a set of blue and visible light emitting diodes can be used with the ultraviolet radiation sources.

In one embodiment, a photocatalyst material can be used with any of the various embodiments to facilitate the irradiation of an object or fluid. For example, the photocatalyst material can undergo a photocatalytic reaction in response to being irradiated by ultraviolet radiation. This photocatalytic reaction can facilitate the removal and suppression of any harmful contaminants present on the surface of an object or a fluid being irradiated the light emitting source(s). The photocatalyst can include $TiO_2$, copper, silver and copper/silver particles, however, other photocatalysts such as, but not including, metal oxides, such as oxides of vanadium, chromium, titanium, zinc, tin, and cerium, can be used to enhance the sterilization and disinfection of object in a variety of applications.

In one embodiment, the photocatalyst can be irradiated by an ultraviolet wavelength in the presence of water vapor to result in formation of hydroxyl group radicals and reactive oxygen species (ROS) that can effectively interact and disrupt the proliferation of microorganisms. In an embodiment the ultraviolet wavelength can be in the range of 360 nm to 380 nm. In an alternative embodiment, the ultraviolet wavelength can be adjusted to be optimal for ROS and hydroxyl group radical formation for each type of photocatalyst used. It is understood that the photocatalyst should be positioned in proximity to the ultraviolet light to ensure that the created ROS and hydroxyl radicals can react with any harmful contaminants that may be present on the surface of object or in a body of fluid.

Figure 12:
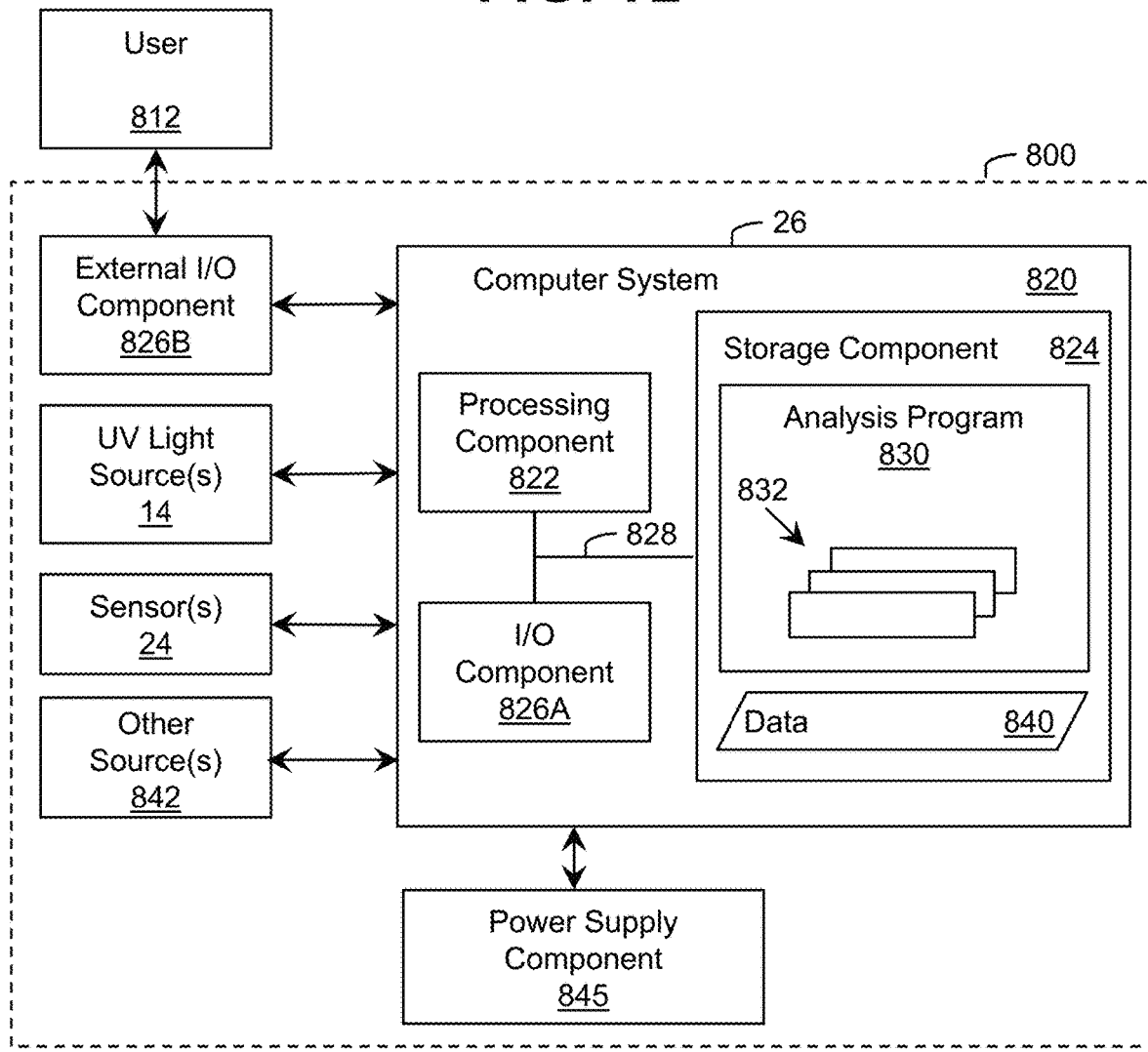
FIG. 12 shows a schematic block diagram representative of an overall processing architecture of a system utilizing an ultraviolet illuminator for irradiating an object or fluid that is applicable to any of the systems described herein according to an embodiment.

FIG. 12 shows a schematic block diagram representative of an overall processing architecture of a system 800 utilizing an ultraviolet illuminator for irradiating an object or fluid that is applicable to any of the systems described herein. In this embodiment, the architecture 800 is shown including the ultraviolet light emitting sources 14 and the sensor(s) 24 for the purposes of illustrating the interaction of all of the components that can be used to provide an ultraviolet treatment.

As depicted in FIG. 12 and described herein, the system 800 can include a control unit 26. In one embodiment, the control unit 26 can be implemented as a computer system 820 including an analysis program 830, which makes the computer system 820 operable to manage the ultraviolet light emitting sources 14 and the sensor(s) 24 in the manner described herein. In particular, the analysis program 830 can enable the computer system 820 to operate the ultraviolet light emitting sources 14 to generate and deliver ultraviolet radiation and process data corresponding to one or more attributes regarding the irradiated item which can be acquired by the sensor(s) 24. The computer system 820 can individually control each ultraviolet light emitting source 14 and sensor 24 and/or control two or more of the ultraviolet light emitting sources and the sensors as a group. Furthermore, the ultraviolet light emitting sources 14 can emit ultraviolet radiation of substantially the same wavelength or of multiple distinct wavelengths, or at any other noted sets of peak wavelengths.

In an embodiment, during an initial period of operation, the computer system 820 can acquire data from at least one of the sensors 24 regarding one or more attributes of the item and generate data 840 for further processing. The data 840 can include information regarding a presence of biological activity (e.g., microorganisms, viruses, bacteria, and/or the like), an amount of radiation (e.g., ultraviolet, infrared, visible, and/or microwave) detected, and/or the like. The computer system 820 can use the data 840 to control one or more aspects of the ultraviolet radiation generated by the ultraviolet light emitting sources 14 during an ultraviolet treatment.

Furthermore, one or more aspects of the operation of the ultraviolet light emitting sources 14 can be controlled or adjusted by a user 812 via an external interface I/O component 826B. The external interface I/O component 826B can be located, for example, on the exterior of any of the aforementioned illuminators and used to allow the user 812 to selectively turn on/off the ultraviolet light emitting sources 14.

The external interface I/O component 826B can include, for example, a touch screen that can selectively display user interface controls, such as control dials, which can enable the user 812 to adjust one or more of: an intensity, scheduling, and/or other operational properties of the set of ultraviolet light emitting sources 14 or other sources (e.g., visible light emitting sources) 842 such as for example, operating parameters, radiation characteristics, and the like. In an embodiment, the external interface I/O component 826B could conceivably include a keyboard, a plurality of buttons, a joystick-like control mechanism, and/or the like, which can enable the user 812 to control one or more aspects of the operation of the set of ultraviolet light emitting sources 14. The external interface I/O component 826B also can include any combination of various output devices (e.g., an LED, a visual display), which can be operated by the computer system 820 to provide status information pertaining to a treatment for use by the user 812. For example, the external interface I/O component 826B can include one or more LEDs for emitting a visual light for the user 812, e.g., to indicate a status of the ultraviolet treatment. In an embodiment, the external interface I/O component 826B can include a speaker for providing an alarm (e.g., an auditory signal), e.g., for signaling that ultraviolet radiation is being generated or that an ultraviolet treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of a treatment. Illustrative aspects of the invention are further described in conjunction with the computer system 820. However, it is understood that the functionality described in conjunction therewith can be implemented by any type of monitoring and/or control system.

When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent computer systems that may perform a process described herein. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 820 includes multiple computing devices, the computing devices can communicate over any type of communications link. Furthermore, while performing a process described herein, the computer system 820 can communicate with one or more other computer systems using any type of communications link. In either case, the communications link can comprise any combination of various types of wired and/or wireless links; any combination of one or more types of networks; and/or utilize any combination of various types of transmission techniques and protocols.

All of the components depicted in FIG. 12 can receive power from a power supply component 845. The power supply component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

While shown and described herein as a system and method, it is understood that aspects of the present invention further provide various alternative embodiments. For example, in one embodiment, the various embodiments of the present invention can include a computer program fixed in at least one computer-readable medium, which when executed, enables a computer system to facilitate the ultraviolet irradiation treatment. To this extent, the computer-readable medium includes program code, such as the analysis program 830, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

In another embodiment, the present invention can provide a method of providing a copy of program code, such as the analysis program 830, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention can implement a method that facilitates an ultraviolet irradiation treatment. This can include configuring a computer system, such as the computer system 820, to implement a method for facilitating the ultraviolet treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
    at least one ultraviolet light emitting source having at least one light emitting side;
    an ultraviolet transparent housing that encapsulates the at least one ultraviolet light emitting source, the ultraviolet transparent housing including an ultraviolet transparent material that transmits ultraviolet light from the at least one ultraviolet light emitting source while preventing humidity from penetrating the ultraviolet transparent housing and damaging the at least one ultraviolet light emitting source, wherein the ultraviolet transparent housing comprises ultraviolet transparent domains forming depressions sunken below an external surface area of the ultraviolet transparent housing to define ultraviolet transparent cellular windows, at least some of the ultraviolet transparent cellular windows having an ultraviolet transparent media enclosed by supporting walls that extend from the sunken depression up to the external surface area of the ultraviolet transparent housing, the ultraviolet transparent domains forming a set of structural elements that provide structural support of the housing to resist a change in shape of the housing; and
    at least one ultraviolet transparent optical element located about the ultraviolet transparent housing interspersed with the ultraviolet transparent material.

2. The system of claim 1, wherein the ultraviolet transparent housing comprises a mesh housing, wherein the ultraviolet transparent cellular windows are integrated within an interlaced structure, each ultraviolet transparent cellular window configured to transmit ultraviolet light there through.

3. The system of claim 2, wherein the ultraviolet transparent cellular windows comprise an ultraviolet transparent fluoropolymer and the interlaced structure comprises a polymer or a fluoropolymer.

4. The system of claim 1, wherein the at least one ultraviolet transparent optical element comprises a set of reflective elements positioned within an interior portion of the ultraviolet transparent housing to provide structural support for the housing.

5. The system of claim 1, wherein the structural elements occupy at least 50% of the external surface area of the ultraviolet transparent housing.

6. The system of claim 1, wherein at least one of the supporting walls comprises a reflective surface that is reflective to ultraviolet light to facilitate ultraviolet transmission and light guiding from the ultraviolet transparent cellular windows.

7. The system of claim 1, wherein the ultraviolet transparent cellular windows have a hexagonal shape and form a hexagonal pattern about the ultraviolet transparent housing.

8. The system of claim 1, wherein some of the ultraviolet transparent domains comprise the least one ultraviolet transparent optical element formed there over while other ultraviolet transparent domains are without the least one ultraviolet transparent optical element formed there over.

9. The system of claim 1, wherein the ultraviolet transparent housing comprises a reflective element formed within an interior portion of the ultraviolet transparent housing to direct ultraviolet light from the at least one ultraviolet light emitting source to the ultraviolet transparent cellular windows.

10. The system of claim 9, wherein the reflective element comprises a cone-shaped element optically coupling the at least one ultraviolet light emitting source to the ultraviolet transparent cellular windows.

11. A system, comprising:
    a set of ultraviolet light emitting sources each having at least one light emitting side to emit ultraviolet light, wherein at least one of the ultraviolet light emitting sources includes an ultraviolet-C (UV-C) light emitting source;
    a cylinder-shaped ultraviolet transparent housing that encapsulates the set of ultraviolet light emitting sources, the ultraviolet transparent housing including:
        an ultraviolet transparent material that transmits ultraviolet light from the set of ultraviolet light emitting sources while preventing humidity from penetrating the ultraviolet transparent housing and damaging the set of ultraviolet light emitting sources;

ultraviolet transparent domains forming depressions sunken below an external surface area of the ultraviolet transparent housing to define ultraviolet transparent cellular windows, at least some of the ultraviolet transparent cellular windows having an ultraviolet transparent media enclosed by supporting walls that extend from the sunken depression up to the external surface area of the ultraviolet transparent housing, the ultraviolet transparent domains forming a set of structural elements that provide structural support of the housing to prevent a change in shape of the housing; and a reflective element positioned within an interior portion of the ultraviolet transparent housing, wherein the reflective element extends axially from one end of the cylinder-shaped ultraviolet transparent housing to an opposing end.

12. The system of claim 11, wherein at least one of the ultraviolet light emitting sources comprises a blue-UV light emitting source configured to operate at a wavelength ranging from 310 nm to 460 nm.

13. The system of claim 11, further comprising at least one visible light source encapsulated within the ultraviolet transparent housing.

14. The system of claim 11, wherein the cylinder-shaped ultraviolet transparent housing comprises a plurality of reflective elements, wherein each of the plurality of reflective elements are separated by a predetermined spacing from each immediately adjacent reflective element.

15. The system of claim 11, wherein at least some ultraviolet transparent domains comprise an ultraviolet transparent optical element formed thereover, the ultraviolet transparent domains and the ultraviolet transparent optical elements formed thereover operate cooperatively to focus ultraviolet light onto a surface of an object.

16. The system of claim 11, wherein the ultraviolet transparent domains are optically connected by ultraviolet transparent waveguiding material that waveguides the ultraviolet light emitted from the set of ultraviolet light emitting sources.

17. A system, comprising:

a set of ultraviolet light emitting sources;

an ultraviolet transparent housing that encapsulates the set of ultraviolet light emitting sources, the ultraviolet transparent housing including an ultraviolet transparent material that transmits ultraviolet light from the set of ultraviolet light emitting sources, wherein the ultraviolet transparent housing comprises ultraviolet transparent domains forming depressions sunken in a surface area of the ultraviolet transparent housing to define ultraviolet transparent cellular windows, each of the ultraviolet transparent cellular windows having an ultraviolet transparent media enclosed by supporting walls that extend from the sunken depression to the surface area of the ultraviolet transparent housing, the ultraviolet transparent domains forming a set of structural elements that provide structural support of the housing to prevent a change in shape of the housing;

at least one ultraviolet transparent optical element located about the ultraviolet transparent housing interspersed with the ultraviolet transparent material; and a control unit configured to control operation of the set of ultraviolet light emitting sources.

18. The system of claim 17, further comprising a user input/output component configured to facilitate user interaction with the control unit.

19. The system of claim 17, further comprising a container, configured to a store at least one object, that is removably coupled to the ultraviolet transparent housing.

20. The system of claim 17, wherein the set of structural elements is configured to support at least one object thereon to facilitate irradiation of a surface of the object by the set of ultraviolet light emitting sources for purposes of disinfection.

* * * * *